US011436806B1

(12) United States Patent
Katz

(10) Patent No.: US 11,436,806 B1
(45) Date of Patent: Sep. 6, 2022

(54) DUAL PERSPECTIVE RENDERING IN VIRTUAL REALITY

(71) Applicant: PENUMBRA, INC., Alameda, CA (US)

(72) Inventor: Howard Steven Katz, Oakland, CA (US)

(73) Assignee: PENUMBRA, INC., Alameda, CA (US)

( * ) Notice: Subject to any disclaimer, the term of this patent is extended or adjusted under 35 U.S.C. 154(b) by 0 days.

(21) Appl. No.: 17/224,235

(22) Filed: Apr. 7, 2021

(51) Int. Cl.
*G06T 19/00* (2011.01)
*A61B 5/00* (2006.01)
*G06F 3/01* (2006.01)

(52) U.S. Cl.
CPC ............ *G06T 19/006* (2013.01); *A61B 5/744* (2013.01); *A61B 5/7425* (2013.01); *G06F 3/011* (2013.01)

(58) Field of Classification Search
None
See application file for complete search history.

(56) References Cited

U.S. PATENT DOCUMENTS

| | | | |
|---|---|---|---|
| 8,471,843 B2 | 6/2013 | Finn et al. | |
| 9,367,950 B1* | 6/2016 | Scranton | G06T 15/10 |
| 9,600,934 B2* | 3/2017 | Odessky | A61B 5/1121 |
| 10,078,917 B1 | 9/2018 | Gaeta et al. | |
| 10,136,214 B2 | 11/2018 | Smus et al. | |
| 10,284,753 B1* | 5/2019 | Naik | G06T 7/596 |
| 10,286,313 B2 | 5/2019 | Goetgeluk et al. | |
| 2014/0188499 A1* | 7/2014 | Bell | G16H 20/30 705/2 |
| 2015/0133820 A1* | 5/2015 | Zohar | A61B 5/1121 600/595 |
| 2016/0199693 A1* | 7/2016 | Vermilyea | A63B 69/3608 700/91 |
| 2017/0153713 A1* | 6/2017 | Niinuma | G09G 5/377 |
| 2017/0278304 A1* | 9/2017 | Hildreth | G06T 19/006 |
| 2017/0326457 A1* | 11/2017 | Tilton | A63F 13/79 |
| 2018/0247023 A1 | 8/2018 | Divine et al. | |
| 2018/0256939 A1* | 9/2018 | Malcolm | A63B 24/0062 |
| 2019/0310757 A1 | 10/2019 | Lee et al. | |
| 2020/0188028 A1* | 6/2020 | Feiner | G16H 50/50 |

(Continued)

OTHER PUBLICATIONS

STAT, "Using VR to transform physical therapy", Aug. 31, 2018, URL: https://www.youtube.com/watch?v=necffi60Fs4 (Year: 2018).*

(Continued)

*Primary Examiner* — David H Chu
(74) *Attorney, Agent, or Firm* — Haley Guiliano LLP

(57) ABSTRACT

Systems and methods are described to render a Live Avatar View third-person view as an overlay of a first person Spectator View, as mirrored from a Virtual Reality headset, in a Dual Perspective View. In some embodiments, a clinician tablet may display Dual Perspective View with a full screen Spectator View, to maximize visibility, and render a translucent avatar from Live Avatar View (LAV) to overlay the Spectator View for simultaneous visibility during a therapy session. Spectator View may be critical to monitor for therapy guidance and an LAV conveys valuable movement and safety data. A translucent avatar overlay and activity cues allows monitoring the avatar from Live Avatar View in a way that would not block the Spectator View or occlude other body parts potentially hidden.

20 Claims, 13 Drawing Sheets

(56) References Cited

U.S. PATENT DOCUMENTS

2020/0319770 A1* 10/2020 Varga .................... G16H 30/20
2021/0034318 A1* 2/2021 Goodman ............. G06F 3/1454

OTHER PUBLICATIONS

Kerckhove, "HTC Vive Tutorial for Unity", Jan. 4, 2019, URL: https://www.raywenderlich.com/9189-htc-vive-tutorial-for-unity (Year: 2019).*

The VR Shop, "Vision Therapy VR (Steam VR)—Valve Index, HTC Vive & Oculus Rift—Gameplay with Commentary", Jan. 22, 2020, URL: https://www.youtube.com/watch?v=BlmBHzx62bU (Year: 2020).*

Rewllio GmbH, "Virtual Reality (VR) and rewellio's innovative stroke therapy software", Dec. 13, 2018, URL: https://www.youtube.com/watch?v=y3tWWIVG0zA (Year: 2018).*

"How to stream/mirror your Vive Focus to an external display or computer", Mar. 16, 2018, URL: https://skarredghost.com/2018/03/16/how-to-stream-mirror-your-vive-focus-to-an-external-display-or-computer/ (Year: 2018).*

Neuro Rehab VR, "Virtual Reality in Physical Therapy by Neuro Rehab VR—Clip from the show Information Matrix TV", Jul. 15, 2019, URL: https://www.youtube.com/watch?v=xGfsAnWu5os (Year: 2019).*

Coopertv, "Cooper is the First Hospital In the World to Use New REAL™ Immersive System for Stroke Rehab", Jan. 23, 2020, URL: https://www.youtube.com/watch?v=lbtO7BGDhTk (Year: 2020).*

PCT International Search Report and Written Opinion for International Application No. PCT/US2022/020521, dated Jul. 6, 2022 (19 pages).

* cited by examiner

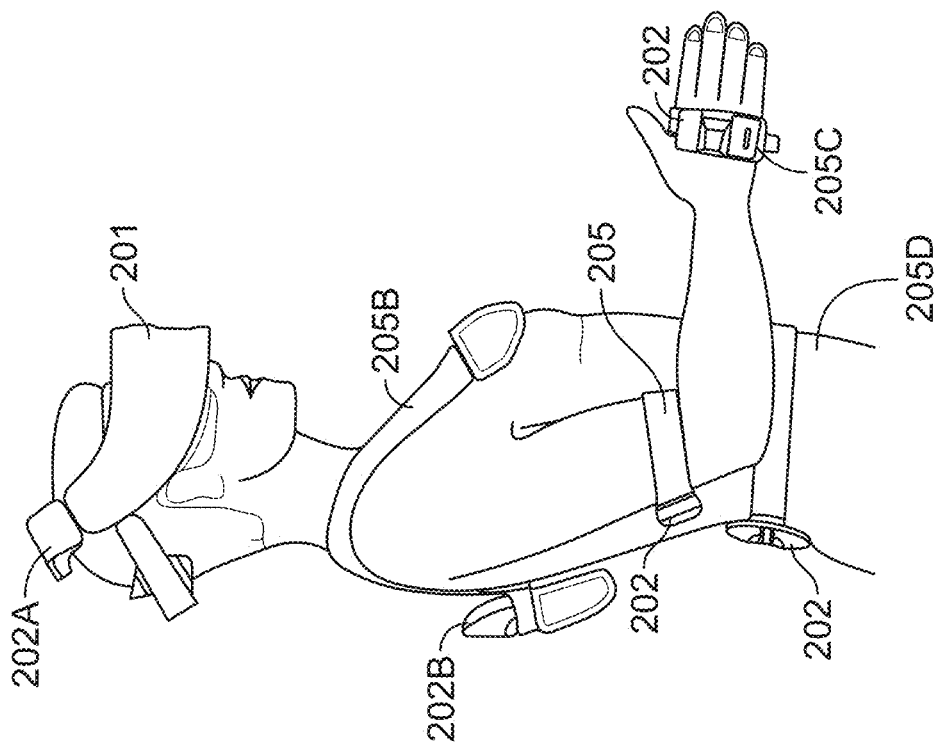
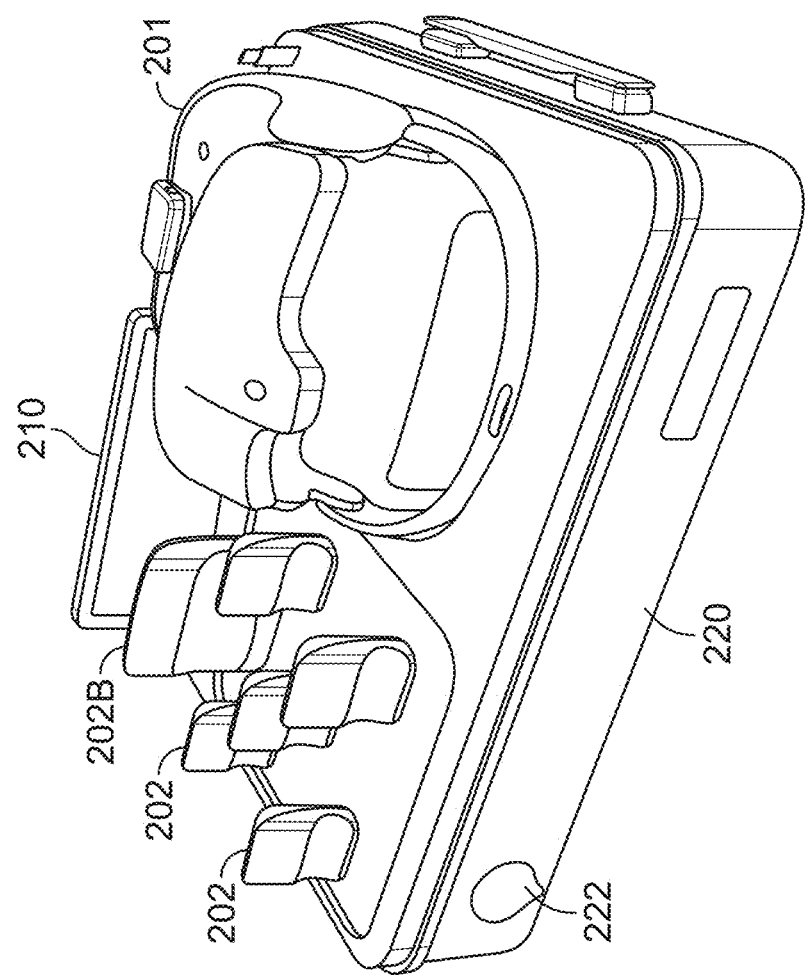
FIG. 7B
FIG. 7A

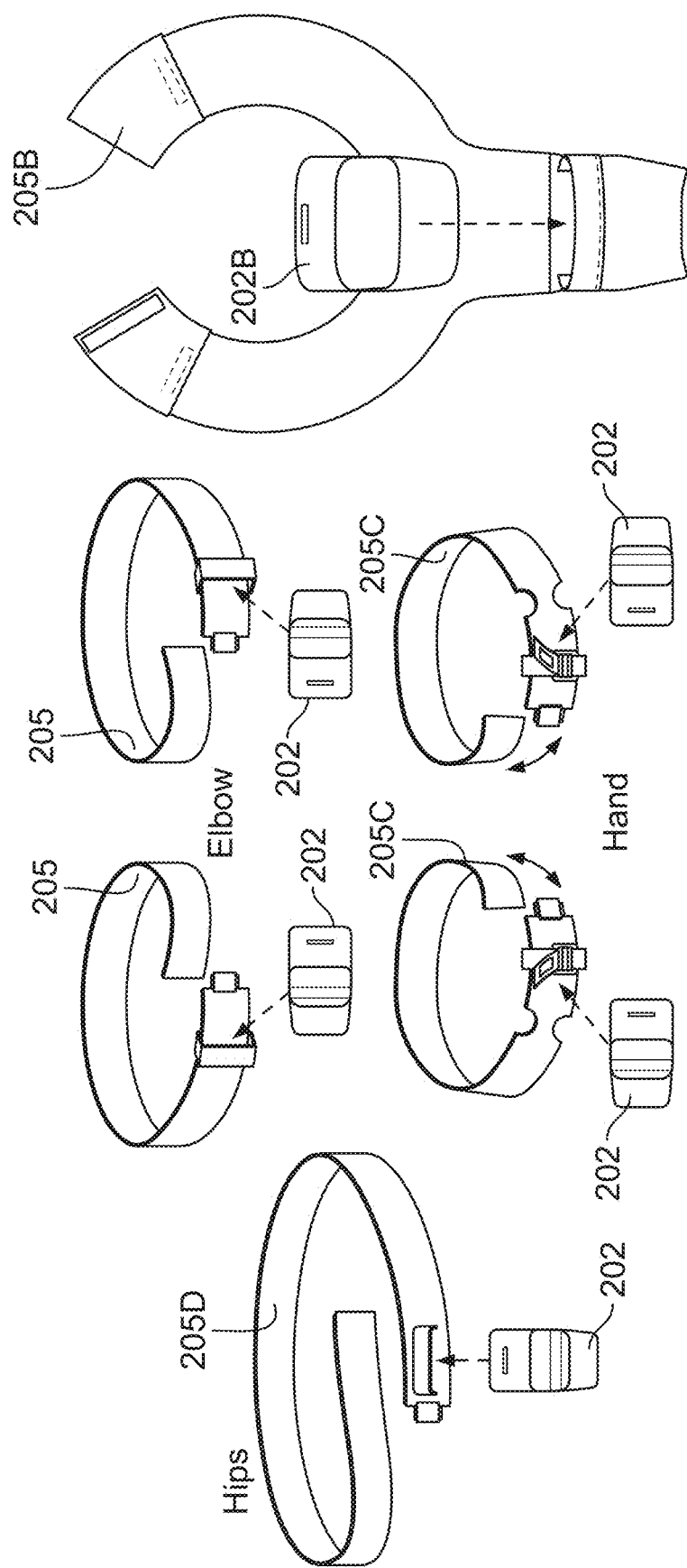

DUAL PERSPECTIVE RENDERING IN VIRTUAL REALITY

BACKGROUND OF THE DISCLOSURE

The present disclosure relates generally to virtual reality systems and more particularly to concurrently rendering an avatar of a patient as an overlay while mirroring the display of a virtual reality headset.

SUMMARY OF THE DISCLOSURE

Virtual reality systems may be used in various applications, including therapeutic activities and games, to assist patients with their rehabilitation and recovery from illness or injury. For safety and proper patient training, a supervising therapist may use a connected display device such as a tablet to present multiple views of the virtual reality (VR) avatar and virtual world to aid in VR therapy activities. As disclosed herein, important avatar views and activity information may be displayed as part of a user interface that maximizes display area efficiency.

VR systems may be designed for use in wellness, health care, and therapy, focusing on physical recovery and neurorehabilitation. For instance, victims of stroke or brain injury may go to physical therapy for treatment to improve, e.g., range of motion, balance, coordination, joint mobility, flexibility, posture, endurance, and strength. Physical therapy may also help with pain management. Generally, for patients, physical therapy is a vital part of recovery and achieving their goals of performing everyday living functions. VR systems can be used to entertain and instruct patients in their movements while emulating practical exercises that may further therapeutic goals.

VR may be used to monitor and help patients retrain their brains and muscles to perform certain tasks that may be difficult in a safe, observable environment. Generally, VR systems can be used to instruct users in their movements while therapeutic VR can replicate practical exercises that may promote rehabilitative goals such as physical development and neurorehabilitation in a safe, supervised environment. For instance, patients with movement disorders may use physical therapy for treatment to improve coordination and mobility. Physical therapy, and occupational therapy, may help patients with movement disorders develop physically and mentally to better perform everyday living functions. VR systems can depict avatars performing actions that a patient with physical and/or neurological disorders may not be able to fully execute.

A VR system may use an avatar of the patient and animate the avatar in the virtual world. Using sensors in VR implementations of therapy allows for real-world data collection as the sensors can capture movements of body parts such as hands, arms, head, neck, back, and trunk, as well as legs and feet in some instances, for the system to convert and animate an avatar in a virtual environment. Such an approach may approximate the real-world movements of a patient to a high degree of accuracy in virtual-world movements. Data from the many sensors may be able to produce visual and statistical feedback for viewing and analysis by doctors and therapists. Generally, a VR system collects raw sensor data from patient movements, filters the raw data, passes the filtered data to an inverse kinematics (IK) engine, and then an avatar solver may generate a skeleton and mesh in order to render the patient's avatar. Typically, avatar animations in a virtual world may closely mimic the real-world movements, but virtual movements may be exaggerated and/or modified in order to aid in therapeutic activities. Visualization of patient movements through avatar animation could stimulate and promote neuron repairs, recovery, and regeneration for the patient. Visualization of patient movements may also be vital for therapists observing in person or virtually.

A VR system used in health care typically requires supervision, such as monitoring and/or guidance by a doctor or therapist. Generally, a health care provider may use a clinician tablet to monitor and control the patient's VR experience. A clinician tablet is typically in wired or wireless communication with a VR head-mounted display (hereinafter, "HMD" or headset) and receives data in real time (or nearly real time). A VR system may be configured for in-person and/or remote observations. A clinician tablet may also feature an application to communicate with a router and remote cloud software configured to authenticate users and store and access information. A clinician tablet may feature a user interface to, for example, monitor patient movement data, session and/or activity data, a mirrored display of the headset display, and a third-person view of the avatar's movements.

"Spectator View" may be a reproduction or mirroring of the visual display in the headset. The display in the patient's headset ("Patient View") typically presents a stereoscopic three-dimensional first-person view of the virtual world through the eyes of the patient's avatar. Spectator View may be, for example, a two-dimensional version of Patient View, displayed on a clinician tablet or even using a separate, larger display screen for multiple therapists or spectators.

Spectator View is important for monitoring by a therapist who may aid the patient in comprehending and performing the therapeutic activity. For instance, a therapist may guide a patient to look at certain features in HMD View that the therapist sees in Spectator View. For proper training and safety, it is vital that a therapist has Spectator View available for monitoring a patient using a therapeutic VR system.

"Live Avatar View" allows a therapist to monitor movements of the patient's avatar to ensure proper interaction with the virtual world, as well as patient safety. Live Avatar View (LAV) may be a third-person view of a rendered three-dimensional avatar configured to mimic a patient's movements based on patient sensor data. LAV may be a three-dimensional rendering of the avatar as displayed on, e.g., a two-dimensional display, such as the clinician tablet. In some instances, LAV may be rendered in real time by the clinician tablet based on skeletal position data relayed from the HMD. The virtual camera angle for LAV may be unfixed, but a default angle may be a view from behind, e.g., to emulate the real-world view of a therapist behind a patient. An avatar in LAV may be a rudimentary avatar rendering without skin, features, or customizations based on, e.g., height/size and weight. For instance, an avatar in LAV may be a featureless blue mannequin that mimics patient movement. In some instances, an avatar in LAV may include cosmetic features similar to the HMD rendering of the avatar. An avatar (or parts of an avatar) in LAV may be rendered as translucent or semi-transparent to provide a three-dimensional representation of the avatar and display body parts in the background that might otherwise be obscured if rendered as opaque. For instance, an avatar in LAV may be a featureless, translucent blue model that mimics patient movement.

A therapist may be able to identify and troubleshoot potential motion issues using LAV. For instance, if a patient moves her arm and the avatar does not mimic the motion, one or more sensors may need adjustment, repair, or battery replacement/recharge. Likewise, if the wrong body part of an avatar moves, such as an avatar's left arm lifting in LAV when the patient moves her right arm, a therapist may identify that the sensor configuration may have an error. In many cases, the solution to sensor errors may be to remove, replace, and restart the sensors, but problems with an avatar moving contrary to patient motion may not be recognized without LAV. A therapist may also be able to monitor the patient's whole body for safety using LAV, monitoring to ensure a patient refrains from injuring a body part. Moreover, with teleconferencing for therapy, using LAV in a virtual therapy session can be a crucial way to remotely supervise and monitor all parts of the patient's body.

During a VR therapy session, a clinician tablet may display one or both of Spectator View and Live Avatar View. In some approaches, Spectator View and LAV may be depicted on different windows of a display and require the supervisor to switch between each of them, never allowing viewing of both views simultaneously. In some approaches, displaying both Spectator View and LAV on the same screen may take up large portions of the screen and cause each display to be too small. For instance, Spectator View and LAV may be depicted side by side in separate video windows on the same tablet screen. Even the larger screens used in tablets suitable for a clinician tablet have limited screen real estate if displaying both Spectator View and LAV simultaneously. A therapist may place the tablet at a non-trivial distance away, e.g., during setup, and the views may be more difficult to observe. Moreover, a clinician tablet may need to display other patient and activity information. There exists a need for a user interface to simultaneously display both Spectator View and LAV, along with patient and activity information, in a way to maximize display size of each.

As disclosed herein, a VR system may be configured to render a Live Avatar View as an overlay of a Spectator View as mirrored from the headset in a "Dual Perspective View." In some embodiments, a clinician tablet may display Dual Perspective View with a full-screen Spectator View to maximize visibility and render a translucent avatar from Live Avatar View to overlay the Spectator View for a therapy session. For example, an LAV avatar may normally be opaque, but in Dual Perspective View the avatar may be rendered as translucent and displayed in an overlay, so the Spectator View is still visible. A Spectator View is important to monitor for therapy guidance, and LAV conveys valuable movement data. A translucent avatar overlay would allow monitoring the avatar from Live Avatar View in a way that would not block the Spectator View or occlude other body parts potentially hidden.

A VR system may generate the Spectator View component of Dual Perspective View in a manner similar to generating Spectator View on a clinician tablet. For instance, an HMD may generate stereoscopic views in each corresponding eye display and relay one of the displays or, e.g., a 2D composite view, to the clinician tablet for display. While a clinician tablet may normally depict Spectator View in a small portion of the tablet screen, when in Dual Perspective View, the Spectator View may have a larger portion or the whole screen available without having to share with a separate LAV window.

An LAV overlay on a tablet screen during Dual Perspective View may be generated in a manner similar to generating a live avatar in a typical LAV window, however it may be rendered as translucent. An LAV avatar may be rendered by a clinician tablet based on skeletal data transmitted from the HMD. In some embodiments, to generate an LAV, applications on the HMD gather sensor data, translate body positions in the real world to a virtual world coordinate system, render a corresponding avatar skeleton, animate the avatar in a three-dimensional (3D) virtual world, and transmit the avatar skeleton data to the clinician tablet. Upon receiving the avatar skeleton data, the tablet renders and animates the avatar, e.g., in a basic form, to demonstrate how the system interprets the collected sensor data. Typically, an LAV window may be displayed adjacent to a Spectator View, causing each window to be shrunk to fit a portion of the tablet screen. In Dual Perspective View, a translucent avatar may be rendered over the Spectator View, and both views can be maximized on the tablet, visible together. In some instances, Dual Perspective View may include activity cues, such as arrow or bubble that may indicate a hint to the therapist supervisor in LAV. Activity cues may comprise result information, such as a heat map indicating a patient's performance in various spatial regions. By superimposing activity cues in LAV and overlaying LAV on Spectator View, Dual Perspective View may be a single focal point and source for therapy session data and visualization. Dual Perspective View may also include, e.g., as part of activity cues, multiple avatars to demonstrate performance, movement range, and/or body positions in prior activity rounds or tasks.

Dual Perspective View may be critical for VR therapy supervision. Allowing a therapist to observe both the Spectator View and the Live Avatar View simultaneously may improve safety and make therapeutic activities more efficient. Also, with teleconferencing for therapy, using a Dual Perspective View in a virtual therapy session allows a remote supervisor to monitor all parts of the patient's body in LAV, while keeping an eye on Spectator View, with both views in full-screen mode simultaneously.

Various systems and methods disclosed herein are described in the context of a therapeutic system for helping patients, such as stroke victims, but this application is only illustrative. Such a VR system may be suitable with, for example, coaching athletics, training dancers or musicians, teaching students, and other activities. For instance, a golf instructor may employ systems and methods disclosed herein to coach a player's swing in a virtual golf match. A drumming teacher may use it to monitor and teach a student practicing on a (virtual) drum set. Such systems and methods disclosed herein may apply to various VR applications. In context of the VR system, the word "patient" may be considered equivalent to a user, participant, student, etc. and the term "therapist" may be considered equivalent to doctor, physical therapist, clinician, coach, teacher, supervisor, or any non-participating operator of the system. A therapist may configure and/or monitor via a clinician tablet, which may be considered equivalent to a personal computer, laptop, mobile device, gaming system, or display. Some disclosed embodiments include a digital hardware and software medical device that uses VR for health care, focusing on physical and neurological rehabilitation. The VR device may be used in a clinical environment under the supervision of a medical professional trained in rehabilitation therapy. In some embodiments, the VR device may be configured for personal use at home, e.g., with remote monitoring. A therapist or supervisor, if needed, may monitor the experience in the same room or remotely. In some cases, a therapist may be physically remote or in the same room as the patient. For instance, some embodiments may need only a remote therapist. Some embodiments may require a remote therapist and/or someone assisting the patient to place or mount the sensors and headset. Generally, the systems are portable and may be readily stored and carried by, e.g., a therapist visiting a patient.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIG. 7A is a diagram of an illustrative system, in accordance with some embodiments of the disclosure;

FIG. 7B is a diagram of an illustrative system, in accordance with some embodiments of the disclosure;

FIG. 8C is a diagram of an illustrative system, in accordance with some embodiments of the disclosure;

DETAILED DESCRIPTION

Figure 1:
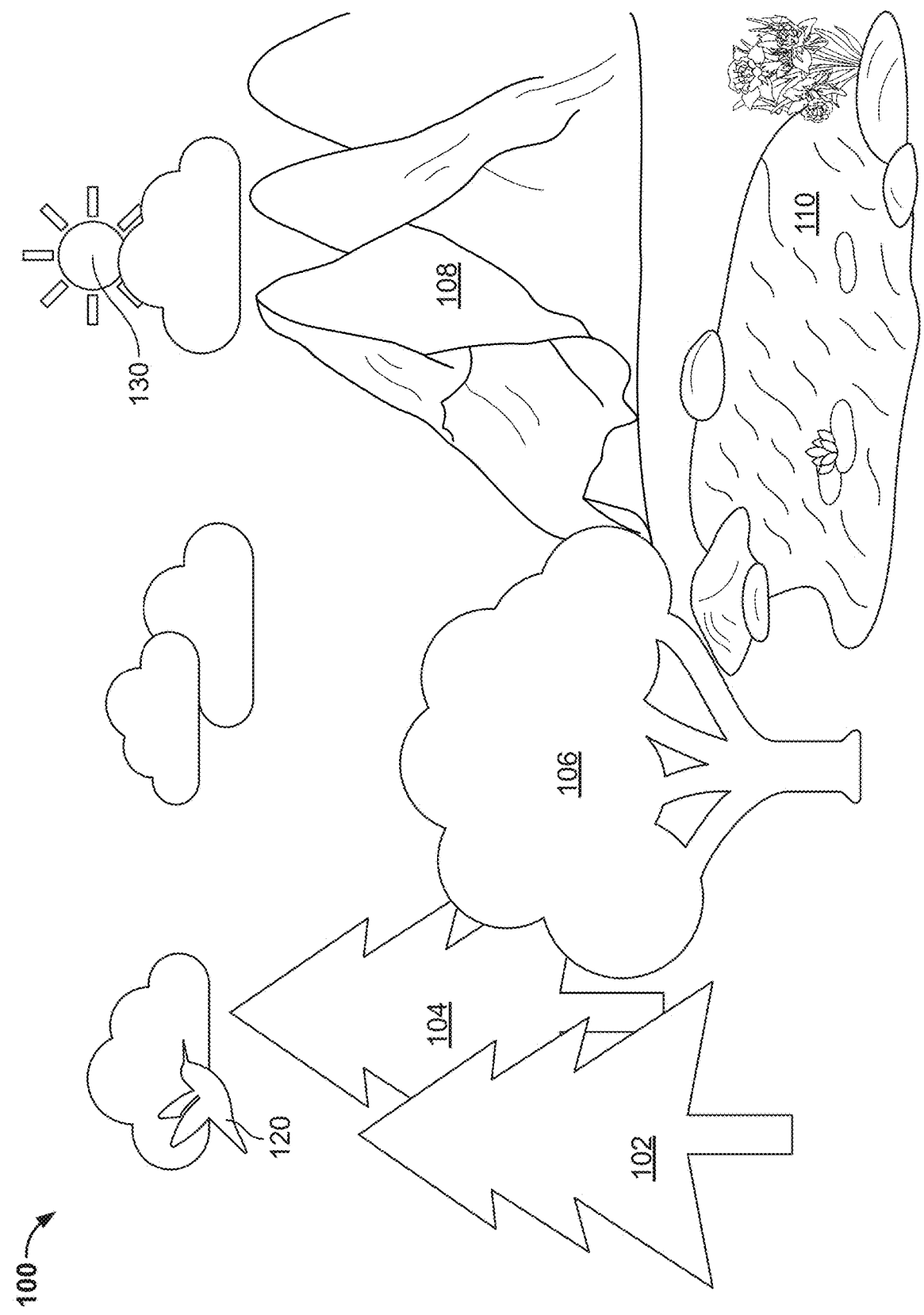
FIG. 1 is an illustrative depiction of a Spectator View, in accordance with some embodiments of the disclosure.

FIG. 1 is an illustrative depiction of a Spectator View in a virtual reality environment, in accordance with some embodiments of the disclosure. By way of a non-limiting example, Scenario 100 of FIG. 1 illustrates a user interface of a virtual reality world as depicted to a spectator, such as a therapist. For instance, a spectator, such as a therapist, may view Scenario 100 and see a reproduction or mirror of a patient's view in the head-mounted display (HMD). Scenario 100 may be referred to as a "Spectator View."

Spectator View mimics the display presented to the patient, also known as "Patient View." Patient View is the view of the VR world from the VR headset. A VR environment rendering engine on an HMD (sometimes referred to herein as a "VR application"), such as the Unreal® Engine, may use the position and orientation data to generate a virtual world including an avatar that mimics the patient's movement and view. Unreal Engine is a software-development environment with a suite of developer tools designed for developers to build real-time 3D video games, virtual and augmented reality graphics, immersive technology simulations, 3D videos, digital interface platforms, and other computer-generated graphics and worlds. A VR application may incorporate the Unreal Engine or another three-dimensional environment developing platform, e.g., sometimes referred to as a VR engine or a game engine. Some embodiments may utilize a VR application, stored and executed by one or more of the processors and memory of a headset, server, tablet and/or other device to render Scenario 100. For instance, a VR application may be incorporated in one or more of head-mounted display 201 and clinician tablet 210 of FIGS. 7A-D and/or the systems of FIGS. 9-10.

Figure 7C:
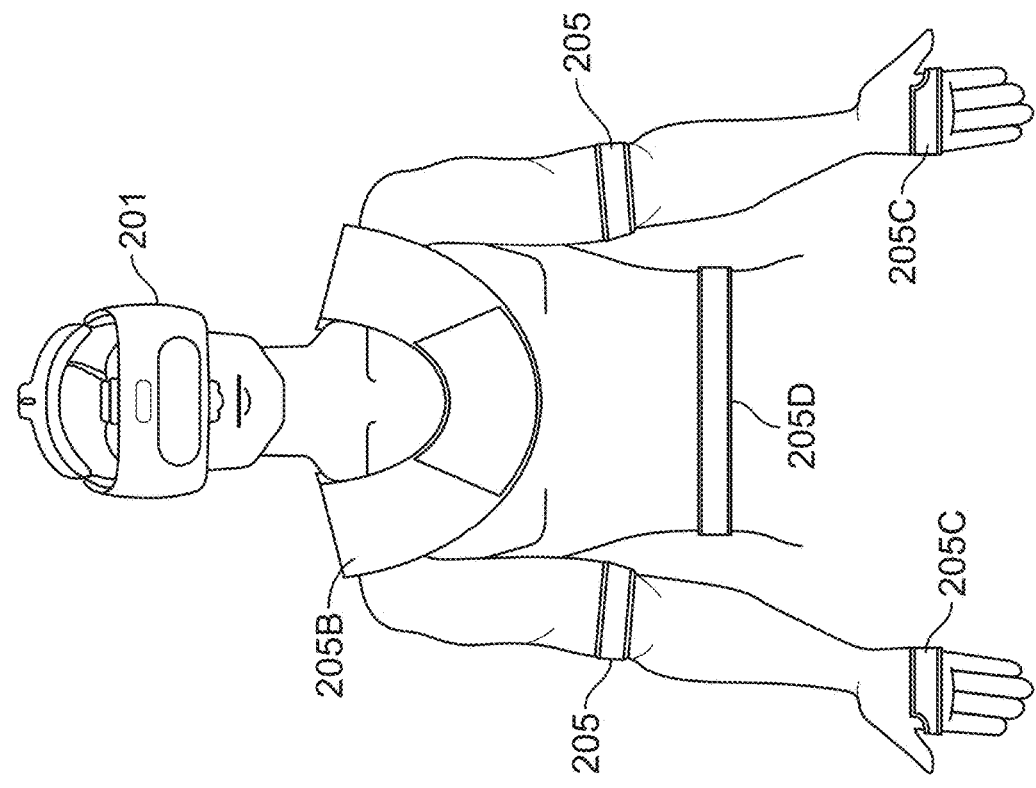
FIG. 7C is a diagram of an illustrative system, in accordance with some embodiments of the disclosure.
Figure 7C:
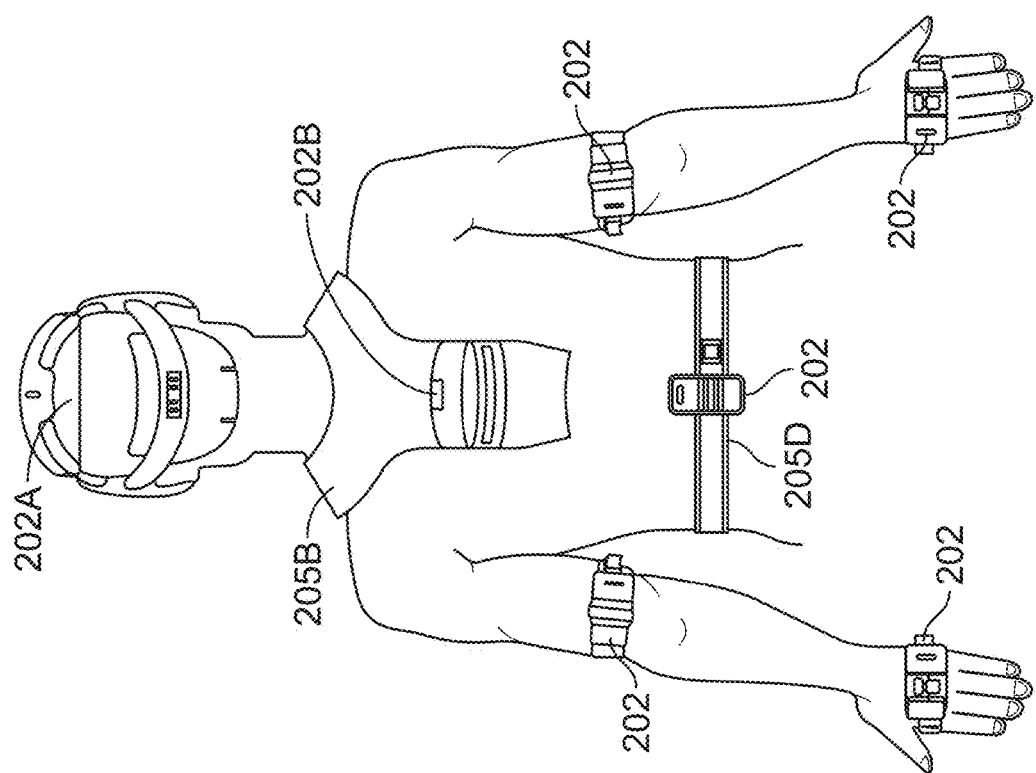
Figure 7D:
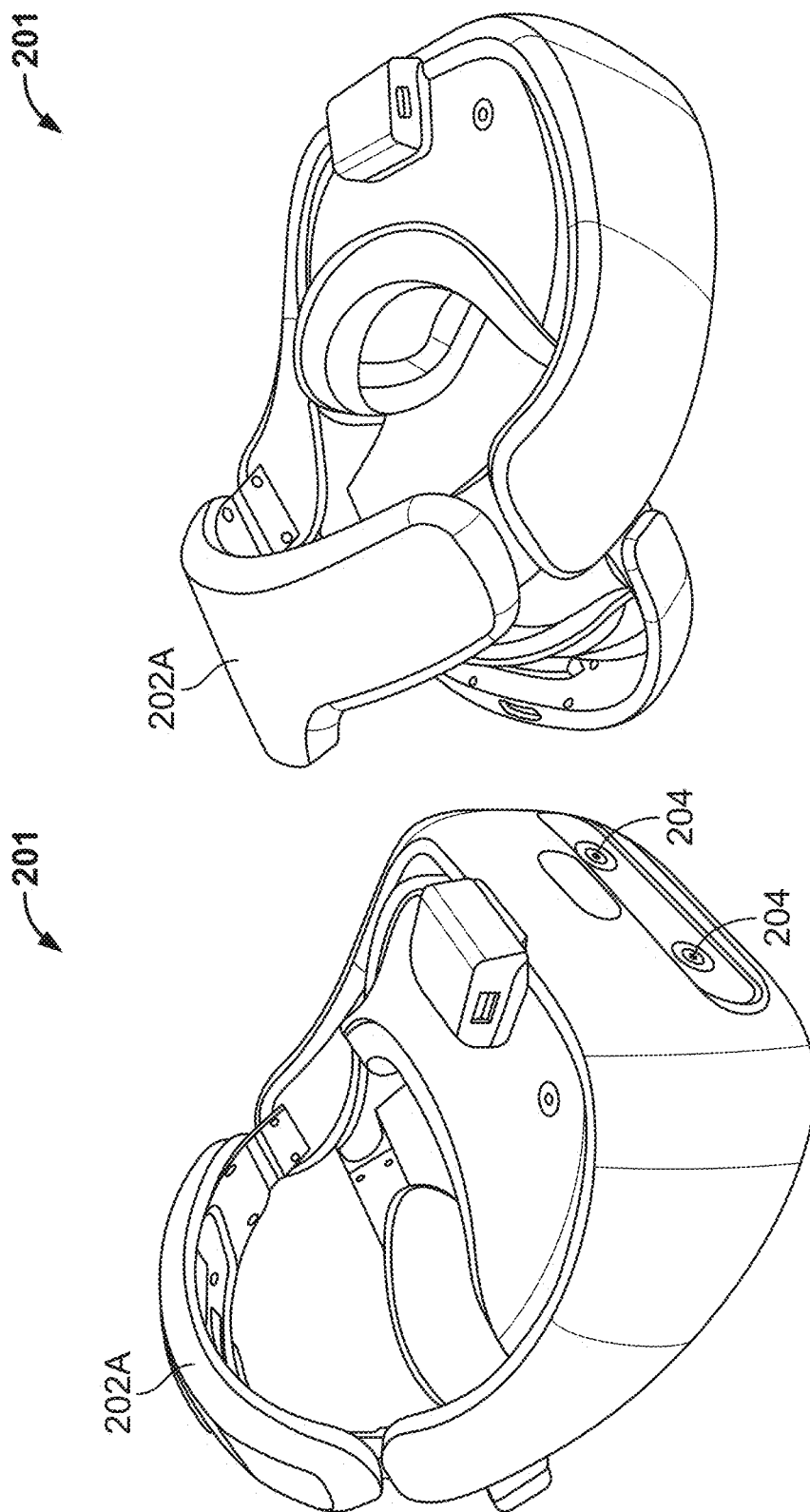
FIG. 7D is a diagram of an illustrative system, in accordance with some embodiments of the disclosure.

Spectator View, of Scenario 100, is a copy of what the patient sees on the HMD while participating in a VR activity, e.g., Patient View. In some embodiments, Scenario 100 may be depicted on a therapist's tablet or display, such as clinician tablet 210 as depicted in FIG. 7A. For instance, Scenario 100 may be a reproduction of Patient View from a participant's HMD, such as headset 201 of FIGS. 7A-D. In some embodiments, an HMD may generate a Patient View as a stereoscopic three-dimensional (3D) image representing a first-person view of the virtual world with which the patient may interact. An HMD may transmit Patient View, or a non-stereoscopic version, as Spectator View to the clinician tablet for display. Spectator View may be derived from a single display, or a composite of both displays, from the stereoscopic Patient View.

Virtual reality systems may be used in various applications, including therapeutic games and activities, to assist patients with their rehabilitation and recovery from illness or injury. Some embodiments may include a variety of experiences that incorporate clinically recognized, existing therapeutic and functional exercises to facilitate motor and cognitive rehabilitation. For instance, games and activities may be used to guide a patient in proper therapeutic experiences.

A VR therapy game might be "Hide and Seek." Depicted in Scenario 100, Hide and Seek is an activity that can be used with or without a displayed avatar tracking the patient's upper body because it primarily relies on head movement and visual scanning ability. Hide and Seek may depict a patient's avatar in a nature setting of a VR world with one or more animals that react to the patient's acknowledgement of them. In some embodiments, Hide and Seek may serve as an introductory activity. For instance, such an activity may be an experience the patient first starts with, e.g., giving a chance for the sensors to be placed on the patient's body and then activating visualization of the avatar. Once the sensors have synced, body parts of the patient's avatar may appear. In some embodiments, Hide and Seek may also be a final activity prior to ending the patient's session, providing time for the therapist to remove the sensors and for the patient to visualize overall progress they made during the session, e.g., in the form of virtual "rewards."

In an activity like Hide and Seek, a patient may "find" bird 120 by turning and rotating their head until gazing in the direction of the bird. In some embodiments, a colored "gaze pointer" may be used as a cursor to indicate direction of view. Sensors on the HMD, as depicted in FIGS. 7A-D as sensor 202A, are used to determine direction of gaze and field of view in the VR world. In Scenario 100, bird 120 appears in the top-left portion of the field of view, above pine trees 102 and 104. Using Spectator View, a therapist may be able to offer hints as to the location of bird 120 to convey that bird 120 appears in the top-left portion of the field of view, above pine trees 102 and 104. When found by the patient, bird 120 will then disappear and reappear in a different location. The activity (or therapist) will instruct the patient to find (e.g., look at, point to, reach towards, etc.) the bird in its new location.

Activities like the Hide and Seek exercise encourage visual scanning of a patient's environment, an important functional ability, and cognitive recognition of nameable animals, objects, and environmental locations in their immediate surrounding. Hide and Seek locations in the world may change and evolve over a number of sessions to provide an experience of logical progression and achievement as the patient continues their course of rehabilitation. Therapists may control the range of locations in which animals appear and wait to be found through "difficulty" settings on the tablet.

In some embodiments, Hide and Seek may incorporate movement of body parts such as reaching out, pointing to, and/or grabbing virtual objects. For instance, the activity (or therapist) may instruct the patient to reach her left hand toward bird 120. The activity may instruct the patient to point her right arm toward mountains 108. The activity may instruct the patient to reach both arms out towards sun 130. The activity may instruct the patient to find a pine tree, such as pine trees 102 and 104. In some embodiments, the patient's avatar is visualized on the HMD and in Spectator View. As the patient performs a task such as reaching or pointing, Scenario 100 may depict an avatar's arm mimicking the patient's movement.

Spectator View allows the supervisor or therapist to see the field of view that the patient sees in the HMD, Patient View. For instance, using a supervisor tablet, Spectator View facilitates giving clues to advance tasks. Spectator View may allow a supervisor to monitor for safety, identifying activity tasks, giving instructions and hints, avoiding VR world distractions, ensuring proper functioning of the VR system, and other potential issues. While Patient View displayed in an HMD is typically stereoscopic, Spectator View is generally not stereoscopic. Spectator View generally is depicted in a large format on a clinician tablet or display to allow better monitoring. For instance, if a patient is participating in an activity like Hide and Seek while a therapist is applying other sensors to the patient's body, then Spectator View may need to be presented on a large display to allow the therapist to monitor from farther away. In some instances, other data, such as patient data, activity data, session data, and timing, may be depicted on a clinician tablet on or in an adjacent portion of a display such as Scenario 100.

Figure 2:
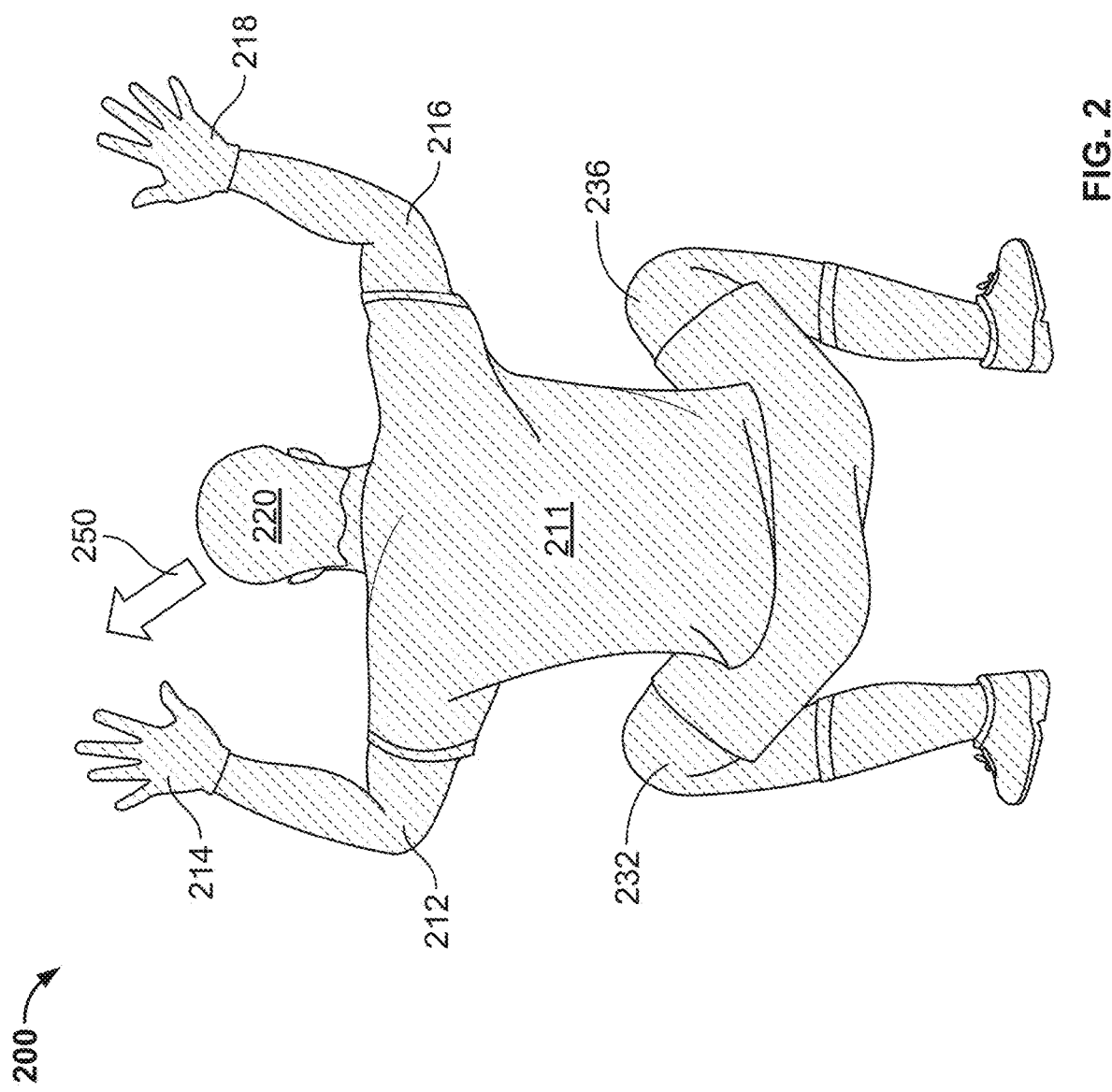
FIG. 2 is an illustrative depiction of a Live Avatar View, in accordance with some embodiments of the disclosure.

FIG. 2 is an illustrative depiction of a Live Avatar View (LAV), in accordance with some embodiments of the disclosure. By way of a non-limiting example, Scenario 200 of FIG. 2 depicts a Live Avatar View that may allow a therapist to monitor movements of the patient's avatar to ensure proper interaction with the virtual world, as well as patient safety. For instance, LAV may be a third-person view of a rendered three-dimensional avatar configured to mimic a patient's movements based on patient sensor data. In some embodiments, Scenario 200 may be depicted on a therapist's tablet or display, such as clinician tablet 210 as depicted in FIG. 7A. For instance, Scenario 200 may be a rendering of avatar 211 based on sensor data collected and analyzed by, e.g., headset 201 of FIGS. 7A-D and transmitted to clinician tablet 210 for rendering. In some embodiments, an HMD may generate avatar skeletal data, as well as activity data, for transmission to the clinician tablet for rendering. A supervisor tablet may be remote in cases of teleconferencing for therapy and connected to the HMD via internet or a virtual network. Using LAV in a virtual therapy session can be a crucial way to remotely supervise and monitor all parts of the patient's body.

Some embodiments may utilize a VR application, stored and executed by one or more of the processors and memory of a headset, server, tablet and/or other device to render avatar 211. For example, some embodiments may incorporate a real-time 3D engine for creating three-dimensional image, three-dimensional interactive graphics and the like, such as Babylon.js, using a JavaScript library for displaying 3D graphics in a web browser via HTML5. In Scenario 200, LAV may be a three-dimensional rendering of avatar 211 as displayed on, e.g., a two-dimensional display, such as the clinician tablet. In some instances, avatar 211 may be rendered in real time by the clinician tablet based on skeletal position data relayed from the HMD. For instance, a VR application may be incorporated in one or more of head-mounted display 201 and clinician tablet 210 of FIGS. 7A-D and/or the systems of FIGS. 9-10. A real-time 3D engine, such as Babylon.js, may render 3D graphics, e.g., in a web browser on a clinician tablet based on received skeletal data from an avatar solver in a three-dimensional environment developing platform (such as the Unreal Engine or any suitable VR environment rendering engine) stored and executed on an HMD.

In Scenario 200, LAV includes avatar 211 with a left hand 214, left arm 212, right hand 218, right arm 216, left leg 232, right leg 236 and head 220. Avatar 211 is depicted sitting down as, for instance, a patient position certain physical therapy may require. Some embodiments may use a virtual camera in LAV with a default viewing angle being a view from behind avatar 211, e.g., to emulate the real-world view of a therapist monitoring from behind a patient. Some embodiments may utilize a virtual camera angle for LAV that is unfixed. In some instances, an avatar in LAV may include cosmetic features like an HMD rendering of an avatar. Avatar 211 may be depicted as a fully detailed human avatar that may be customized to mimic the patient. In some embodiments, avatar 211 may be depicted as a rudimentary avatar rendering without skin, features, or customizations based on, e.g., height, weight, and/or sizes of body parts. For instance, avatar 211 may be a featureless blue mannequin that mimics patient movement. Limiting cosmetic features of avatar 211 may be an efficient use of resources for rendering to a display such as a clinician tablet.

Movements of body parts of avatar 211, such as left hand 214, left arm 212, right hand 218, right arm 216, left leg 232, right leg 236 and head 220, may be calculated based on data originating from multiple sensors worn by a patient. Some embodiments may translate sensor data to skeletal data at the HMD prior to transmission to the clinician tablet. Sensor data may be originally transmitted by sensors to the HMD as part of an exemplary VR system such as sensors 202 depicted in FIGS. 7A-D or FIGS. 8A-C or sensor 902 depicted in FIGS. 9-10. For instance, as depicted in FIG. 8B, wireless sensor module 202 (e.g., sensor or WSM) may be worn as strapped to the back of one or more hands. Sensor 202 is equipped with mechanical and electrical components that measure position and orientation in physical space to be translated for creating a virtual environment. In some embodiments, multiple sensors 202 may be placed on a patient, for example, just above each elbow, strapped to the back of each hand, and at the pelvis, as well as sensors placed on the back and in a head-mounted display (HMD) as depicted, for example, in FIGS. 7B-C. Each sensor 202 may track movement along six degrees of freedom. Body movements may be measured in one or more of the six degrees of movement for translation and depiction, e.g., in a virtual world or in LAV.

In virtual reality, sensors may be used to collect data on physical movement of the patient in order to convert such movement into animation of a VR avatar representing the user such as avatar 211. Converting sensor data to avatar motion may also enable control of aspects of the software, such as performing tasks in a game or activity. Virtual reality systems may be used in various applications, including therapeutic games and activities, to assist patients with their rehabilitation and recovery from illness or injury. For instance, in a game where birds are lifted by the patient, the sensor data from the patient lifting her arm may be used to animate the avatar lifting a bird as well as animate the bird moving from one level to another level.

Generally, an avatar solver employs inverse kinematics (IK) and a series of local offsets to constrain the skeleton of the avatar to the position and orientation of the sensors. The skeleton then deforms a polygonal mesh to approximate the movement of the sensors. An avatar includes virtual bones and comprises an internal anatomical structure that facilitates the formation of limbs and other body parts. A real-time 3D engine, such as Babylon.js, may render 3D graphics, e.g., in a web browser on a clinician tablet based on received skeletal data.

A position of avatar 211 at a given point in time may be rendered by utilizing a skeleton rig, whereby the bones of the skeleton rig are manipulated in the rendering process to position the avatar in a position similar to the user's own position. For instance, LAV on a clinician tablet may use a rigged skeleton and mesh in Babylon.js, applied in real time and based on skeletal positions and rotations transmitted from the HMD. In some embodiments, systems and methods of the present disclosure may animate an avatar by blending the nearest key poses in proportion to their proximity to the user's tracked position, e.g., vertex animation. In some embodiments, a combination of vertex animation and skeletal animation may be applied to render an avatar.

Using LAV, a therapist may be able to identify and troubleshoot potential motion issues. For instance, if a patient moves his right arm and arm 218 does not mimic the motion, one or more sensors may need adjustment, repair, or battery replacement/recharge. Likewise, if the wrong body part of an avatar moves, such as left arm 212 lifting in LAV when the patient moves her right arm, a therapist may identify that the sensor configuration may have an error. In many cases the solution to sensor errors may be to remove, replace, and restart the sensors, but some problems with avatar 211 moving contrary to patient motion may not be recognized without LAV of Scenario 200. In some instances, other data, such as patient data, activity data, session data, and timing, may be depicted on a clinician tablet on or in an adjacent portion of a display such as Scenario 200.

Scenario 200 may also include activity arrow 250 as, for instance, an activity cue. In some embodiments where a patient is participating in a therapeutic VR game, activity cues, such as activity arrow 250, may indicate a hint to the therapist supervisor in LAV. For instance, in an activity where birds are supposed to be found or pointed to by the patient, such as depicted in Scenario 100, activity arrow 250 is displayed in LAV so that a therapist supervisor may relay a direction for the patient to, e.g., aim head 220 up and to the left. Activity arrow 250 may indicate any available direction and may be two-dimensional or three-dimensional. For instance, if a camera angle for LAV moves and avatar 211 rotates, activity arrow 250 may rotate three-dimensionally, too, in order to maintain relative direction while a therapist looks at a specific avatar body part. In some cases, activity arrow 250 may remain stationary even while if avatar 211 or head 220 rotates, to quickly convey a static direction to look to the supervisor. Activity arrow 250 may vary in size depending on required displacement magnitude for the patient to move her head. In some embodiments, there may be more than one activity arrow 250, e.g., with indications of priority with size, color, or annotations. For instance, a green activity arrow 250 may indicate the patient is supposed to look in a first direction, while a yellow activity arrow 250 may indicate the patient should look in a second direction afterwards. In some embodiments, activity cues, like activity arrow 250, may be one or more other shapes or graphics to indicate, in LAV viewed by a therapist, a direction where a patient should look or move one or more body parts. Along with LAV, activity cues can be an important tool for therapists to guide therapy. LAV may also include, e.g., as part of activity cues, multiple avatars to demonstrate performance, movement range, and/or body positions in prior activity rounds or tasks. In some embodiments, LAV may include a recording of a prior rendering, e.g., more transparent or lighter, of an avatar performing the same task on top of or next to the live rendering. For instance, LAV may display a prior rendering a patient reaching (e.g., towards a virtual bird or sun) on top of the real-time rendering of an activity for the therapist or supervisor to compare flexibility or range of motion. In some embodiments, measurement data such as position and rotation data may be provided in LAV for therapist viewing and comparison.

Figure 3:
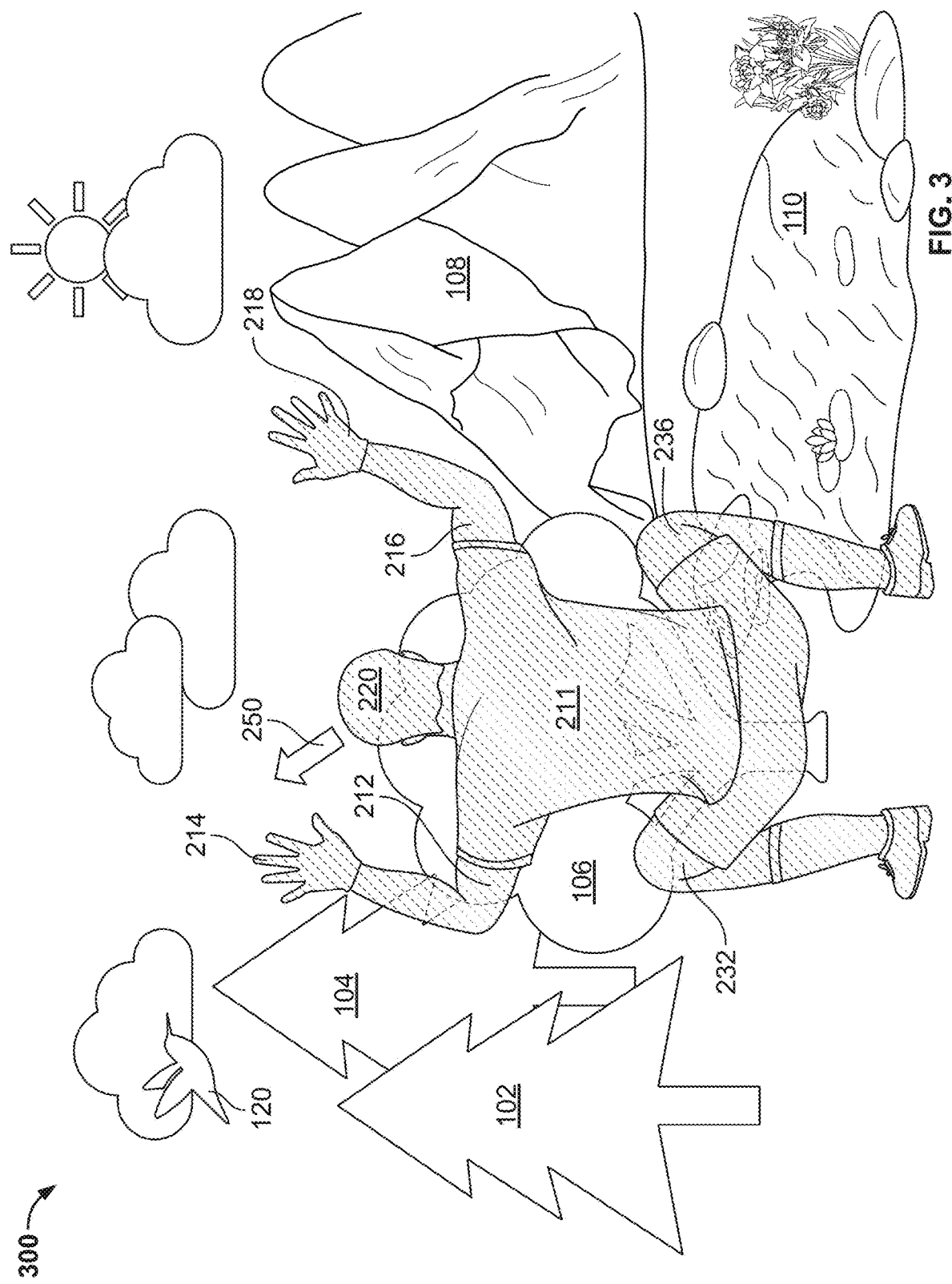
FIG. 3 is an illustrative depiction of a Dual Perspective View, in accordance with some embodiments of the disclosure.

FIG. 3 is an illustrative depiction of a Dual Perspective View in a virtual reality environment, in accordance with some embodiments of the disclosure. By way of a non-limiting example, Scenario 300 of FIG. 3 illustrates a user interface of a virtual reality world as depicted to a spectator overlaid with a third-person view of a rendered three-dimensional avatar configured to mimic a patient's movements based on patient sensor data. Scenario 300 depicts Live Avatar View of Scenario 200 overlaying Spectator View of Scenario 100 to create a Dual Perspective View.

In some embodiments, Scenario 300 may be depicted on a therapist's tablet or display, such as clinician tablet 210 as depicted in FIG. 7A. For instance, Scenario 300 may comprise a rendering of the virtual world from an HMD, such as headset 201 of FIGS. 7A-D, overlaid with a rendering of avatar 211 based on sensor data collected and analyzed by the HMD and transmitted to clinician tablet 210 for rendering. In some embodiments, an HMD may generate and transmit a Spectator View, as well as generate and transmit avatar skeletal data to a clinician tablet for rendering a Live Avatar View. For instance, a clinician tablet may receive a Spectator View and avatar skeletal data and render the skeletal data as an LAV overlaying the Spectator View to create a Dual Perspective View. Dual Perspective View includes the best features of LAV and Spectator View in order to maximize screen space and facilitate safety and proper instruction for a VR session.

As depicted in Scenario 300, a Dual Perspective View may comprise a translucent avatar 211 from LAV rendered over the Spectator View. In some embodiments, avatar 211 is translucent and Spectator View is generally visible behind avatar 211. A therapist or supervisor would still be able to see objects behind avatar 211 and direct the patient to look or point to the objects. For instance, tree 106 is visible behind avatar 211 in Scenario 300, and a therapist may ask a patient to look at or reach towards tree 106. In some instances, such as a therapeutic activity session of "Hide and Seek," bird 120 may be depicted as having moved toward tree 106, behind avatar 211, but would it still be visible behind translucent avatar 211. Activity arrow 250 and other information from LAV may be depicted as translucent. In some embodiments, overlaying may include layering to distinguish views. For instance, layering a different color, e.g., gray, over Spectator View may better distinguish LAV from Spectator View. Layering may use a gray mask with low alpha channel to gray out the bottom layer. In some embodiments, the layering color and opacity may be changed by the supervisor adjusting a setting.

Figure 4:
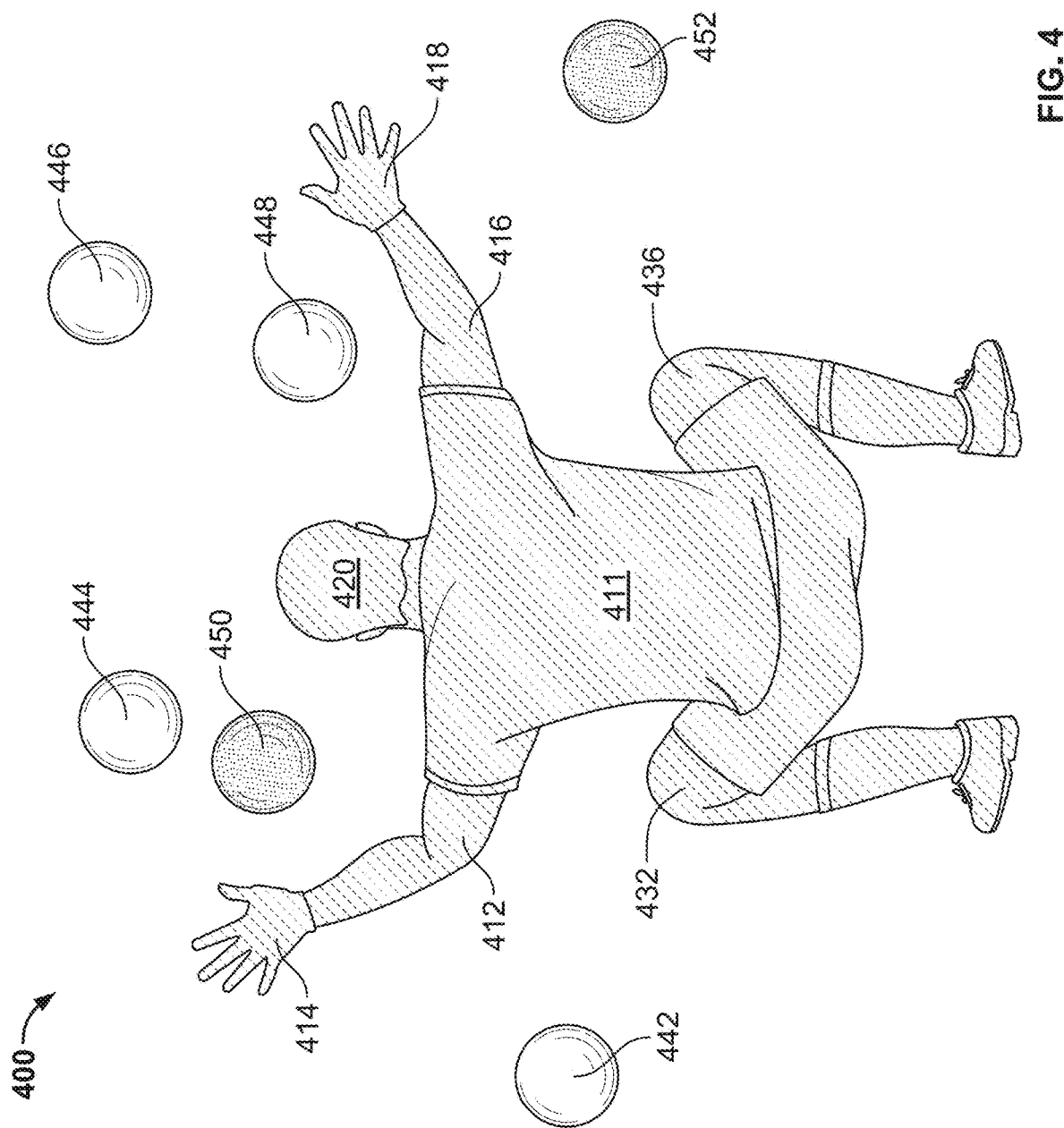
FIG. 4 is an illustrative depiction of activity cues in Live Avatar View, in accordance with some embodiments of the disclosure.

FIG. 4 is an illustrative depiction of a Live Avatar View (LAV), in accordance with some embodiments of the disclosure. By way of a non-limiting example, Scenario 400 of FIG. 4 depicts a Live Avatar View that may allow a therapist to monitor movements of the patient's avatar to ensure proper interaction with the virtual world, as well as patient safety. Scenario 400 includes bubbles 442-452 as activity cues for the therapist or supervisor. In some embodiments, Scenario 400 may be depicted on a therapist's tablet or display, such as clinician tablet 210 as depicted in FIG. 7A. For instance, Scenario 400 may be a rendering of avatar 411 based on sensor data collected and analyzed by, e.g., headset 201 of FIGS. 7A-D and transmitted to clinician tablet 210 for rendering.

In some embodiments, an HMD may generate avatar skeletal data, as well as activity data, for transmission to the clinician tablet for rendering. Some embodiments may utilize a VR application, stored and executed by one or more of the processors and memory of a headset, server, tablet and/or other device to render avatar 411. For example, some embodiments may incorporate a real-time 3D engine, such as Babylon.js, using a JavaScript library for displaying 3D graphics in a web browser via HTML5. In Scenario 400, LAV may be a three-dimensional rendering of avatar 411 as displayed on, e.g., a two-dimension display, such as the clinician tablet. In some instances, avatar 411 may be rendered in real time by the clinician tablet based on skeletal position data relayed from the HMD. For instance, a VR application may be incorporated in one or more of head-mounted display 201 and clinician tablet 210 of FIGS. 7A-D and/or the systems of FIGS. 9-10. A real-time 3D engine, such as Babylon.js, may render 3D graphics, e.g., in a web browser on a clinician tablet based on received skeletal data from an avatar solver in the Unreal Engine stored and executed on an HMD.

In Scenario 400, LAV includes avatar 411 with a left hand 414, left arm 412, right hand 418, right arm 416, left leg 432, right leg 436 and head 420. Avatar 411 is depicted sitting down. Movements of body parts of avatar 411, such as left hand 414, left arm 412, right hand 418, right arm 416, left leg 432, right leg 436 and head 420, may be calculated based on skeletal data translated from sensor data. Scenario 400 uses a virtual camera in LAV with a viewing angle view from behind avatar 411, e.g., to emulate the real-world view of a therapist monitoring from behind a patient.

Scenario 400 depicts an LAV of a patient participating in a therapeutic goal-defending game such as attempting to stop soccer penalty kicks. In Scenario 400, a patient is tasked with grabbing or blocking virtual balls as they are projected towards him. In the game, a patient may use left hand 414, left arm 412, right hand 418, and or right arm 416, to block a ball. Scenario 400 depicts bubbles 442-452 as prior projected balls, with a position relative to avatar 411 depicted in LAV. Scenario 400 may be considered a heat map for successful block attempts in the virtual activity. Of bubbles 442-452, shaded bubbles 450 and 452 indicate balls that have passed by the patient avatar in the game, while unshaded bubbles 442-448 indicate balls that were blocked. Looking at an LAV, such as one depicted in Scenario 400, a supervisor or therapist can quickly identify progress of the patient's activity. In some embodiments, an activity cue such as bubble 444 may indicate an upcoming ball so that, for instance, a therapist may warn the patient where to look or anticipate to reach. Some embodiments may depict a prior rendering of an avatar in LAV for comparison of movement, e.g., flexibility and range of motion.

Figure 5:
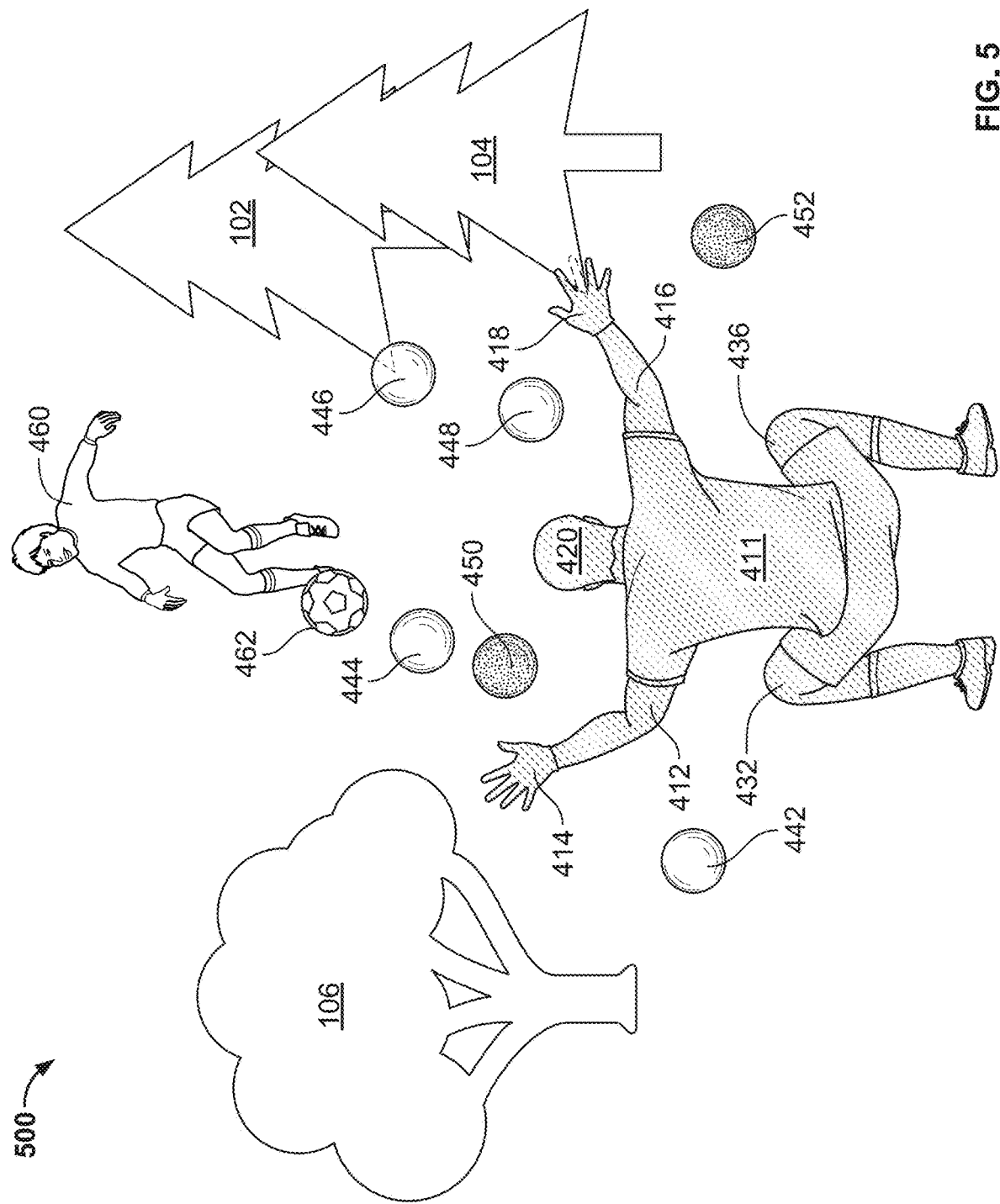
FIG. 5 is an illustrative depiction of activity cues in Dual Perspective View, in accordance with some embodiments of the disclosure.

FIG. 5 is an illustrative depiction of activity cues in Dual Perspective View in a virtual reality environment, in accordance with some embodiments of the disclosure. Scenario 500 depicts LAV overlaid on a Spectator View with each view depicting a therapeutic goal-defending game such as attempting to stop soccer penalty kicks. Like Scenario 400, in Scenario 500, a patient is tasked with grabbing or blocking virtual balls as they are kicked towards him. By way of a non-limiting example, Scenario 500 of FIG. 5 illustrates a user interface of a virtual reality world as depicted to a spectator overlaid with a third-person view of a rendered three-dimensional avatar configured to mimic a patient's movements based on patient sensor data. Scenario 500 depicts a Live Avatar View of Scenario 400 overlaying a Spectator View (that may include background elements from Scenario 100) to create a Dual Perspective View.

In some embodiments, Scenario 500 may be depicted on a therapist's tablet or display, such as clinician tablet 210 as depicted in FIG. 7A. For instance, Scenario 500 may comprise a rendering of the virtual world from an HMD, such as headset 201 of FIGS. 7A-D, overlaid with a rendering of avatar 411 based on sensor data transmitted to clinician tablet 210, from HMD 201, for rendering. In some embodiments, for instance, a clinician tablet may receive a Spectator View and avatar skeletal data and render the skeletal data as an LAV overlaying the Spectator View to create a Dual Perspective View. Dual Perspective View includes the best features of LAV and Spectator View in order to maximize screen space and facilitate safety and proper instruction for a VR session.

As depicted in Scenario 500, a Dual Perspective View may comprise a translucent avatar 411 from LAV rendered over the Spectator View. In some embodiments, avatar 411 is translucent and Spectator View is generally visible behind avatar 411. A therapist or supervisor would still be able to see objects rendered behind avatar 411 and instruct the patient to look or point to the objects. For instance, tree 104 is visible behind right hand 418 in Scenario 500 and a therapist may ask a patient to look at or reach towards tree 106. In some embodiments, overlaying may include layering, e.g., with gray, to aid in distinguish views.

Scenario 500 depicts LAV overlaid on a Spectator View for a goal-defending game where a patient is tasked with grabbing or blocking virtual balls as they are kicked towards him. Like Scenario 400, Scenario 500 also depicts bubbles 442-452 as prior projected balls, with a position relative to avatar 411 depicted in LAV mode of the Dual Perspective View. Using Dual Perspective View, bubbles may need to be colored or shaded, e.g., in addition to their translucency, in order to be more visible in Spectator View layer. Looking at a Dual Perspective View such as the view in Scenario 500, a supervisor or therapist can quickly identify progress of the patient's activity from LAV, as well as see the Spectator View. In some embodiments, additional activity cues, including bubbles or arrows, may indicate an upcoming object so that, for instance, a therapist may warn a patient where to look.

Figure 6:
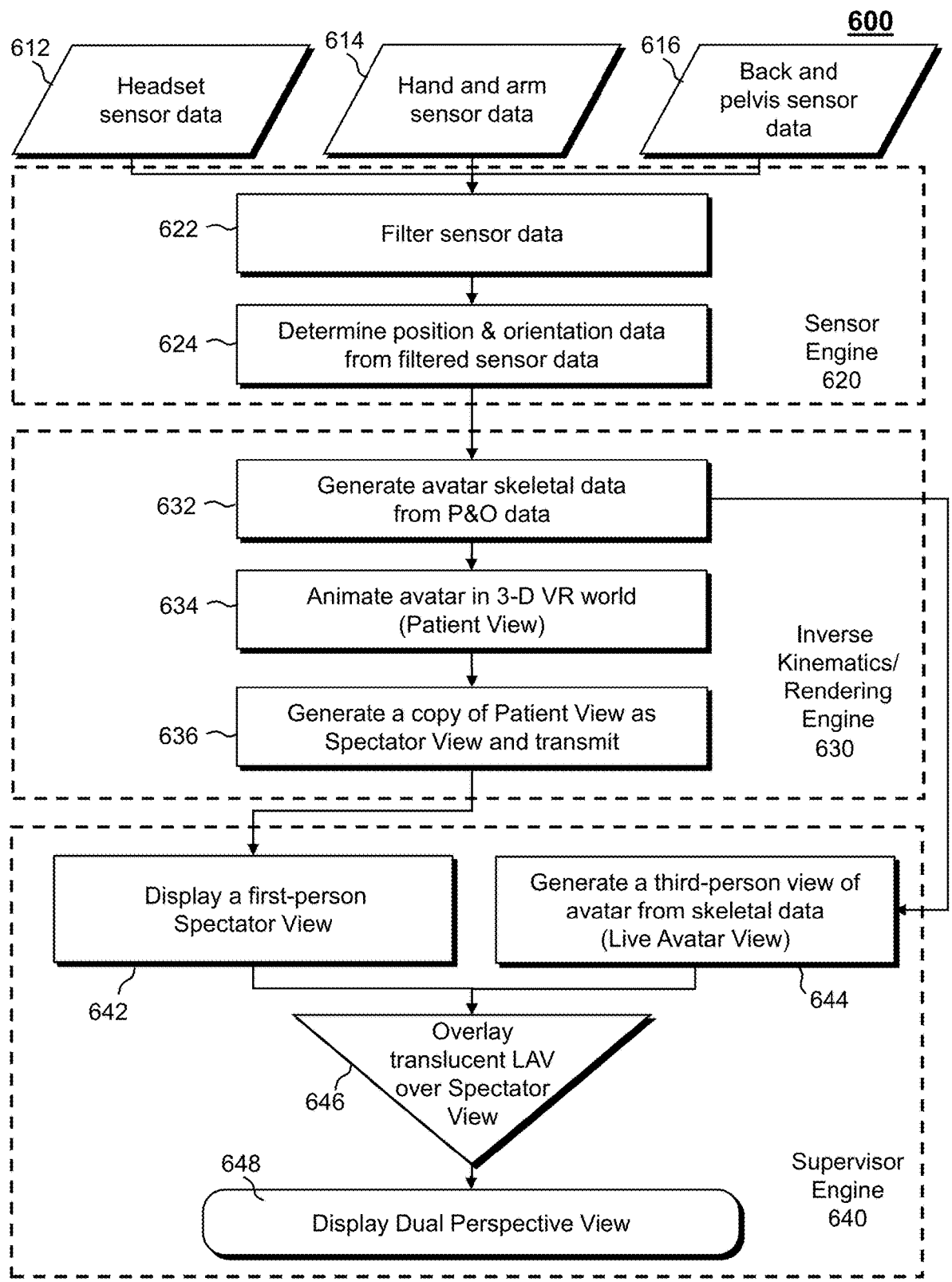
FIG. 6 depicts an illustrative flowchart of a process for generating Dual Perspective View, in accordance with some embodiments of the disclosure.

FIG. 6 depicts an illustrative flowchart of a process for generating Dual Perspective View, in accordance with some embodiments of the disclosure. Process 600 includes steps for receiving sensor data input, generating a Patient View, generating a Live Avatar View, and overlaying the views. Some embodiments may utilize one or more of a sensor engine, an inverse kinematics (IK) solver with a rendering engine (IK/rendering engine), and a supervisor engine, e.g., as part of a VR application, stored and executed by one or more of the processors and memory of a headset, server, tablet and/or other device carrying out the steps of process 600 depicted in the flowchart of FIG. 6. For instance, sensor engine 620, IK/rendering engine 630, and a supervisor engine 640 may be incorporated in one or more of head-mounted display 201 and clinician tablet 210 of FIGS. 7A-D and/or the systems of FIGS. 9-10.

At each of input 612, input 614, and input 616 sensors may transmit captured sensor data as input to sensor engine 620. Sensor data may be transmitted by a sensor as part of an exemplary VR system such as sensor 202 depicted in FIGS. 7A-D or FIGS. 8A-C or sensor 902 depicted in FIGS. 9-10. In some embodiments, multiple sensors 202 may be placed on a patient, for example, just above each elbow, strapped to the back of each hand, and at the pelvis, as well as sensors placed on the back and in a head-mounted display (HMD) as depicted, for example, in FIGS. 7B-C.

At input 612, headset sensor data may be captured and input. Headset sensor data may be captured, for instance, by a sensor on the HMD, such as sensor 202A on HMD 201 as depicted in FIGS. 7A-D. Sensors may transmit data wirelessly or via wire, for instance, to a data aggregator or directly to the HMD for input. Additional sensors, placed at various points on the body, may also measure and transmit/input sensor data.

At input 614, hand and arm sensor data may be captured and input. Hand and arm sensor data may be captured, for instance, by sensors affixed to a patient's hands and arms, such as sensors 202 as depicted in FIGS. 7A-C and 8A-C. Sensor data from each hand and each arm may be transmitted and input separately or together.

At input 616, back and pelvis sensor data may be captured and input. Back and pelvis sensor data may be captured, for instance, by sensors affixed to a patient's back and pelvis, such as sensors 202 and 202B as depicted in FIGS. 7A-C and 8A-C. Sensor data from each of the back and pelvis sensors may be transmitted and input separately or together.

With each of inputs 612, 614, and 616, data from the sensors may be input into sensor engine 620. Sensor data may comprise location and rotation data in relation to a central sensor such as a sensor on the HMD or a sensor on the back in between the shoulder blades. For instance, each sensor may measure a three-dimensional location and measure rotations around three axes. Each sensor may transmit data at a predetermined frequency, such as 200 Hz.

At step 622, sensor engine 620 filters sensor data. For instance, the sensor engine may process sensor data to reduce size. In some embodiments, sensor 202 may pre-filter or clean "jitter" from raw sensor data prior to transmission. In some embodiments, sensor 202 may capture data at a high frequency (e.g., 200 Hz) and transmit a subset of that data, e.g., transmitting captured data at a lower frequency.

At step 624, sensor engine 620 determines position and orientation (P&O) data from filtered sensor data. For instance, data may include a location in the form of three dimensional coordinates and rotational measures around each of the three axes. Sensor engine 620 may produce virtual world coordinates from these sensor data to eventually generate skeletal data for an avatar. In some embodiments, sensors may feed sensor engine 620 raw sensor data. In some embodiments, sensors may input filtered sensor data into sensor engine 620. The P&O data is passed to IK/rendering engine 630.

At step 632, IK/rendering engine 630 generates avatar skeletal data from the determined P&O data. Generally, a solver employs inverse kinematics (IK) and a series of local offsets to constrain the skeleton of the avatar to the position and orientation of the sensors. The skeleton then deforms a polygonal mesh to approximate the movement of the sensors. An avatar includes virtual bones and comprises an internal anatomical structure that facilitates the formation of limbs and other body parts. Skeletal hierarchies of these virtual bones may form a directed acyclic graph (DAG) structure. Bones may have multiple children, but only a single parent, forming a tree structure. Two bones may move relative to one another by sharing a common parent. The skeletal data is passed to supervisor engine 640.

At step 634, IK/rendering engine 630 animates the avatar in a three-dimensional VR world, also known as "Patient View." For instance, a rendering engine, e.g., IK/rendering engine 630, will use skeletal data from the IK solver to render and animate an avatar. Virtual skin may surround the virtual bones as an exterior surface representation of the avatar. A three-dimensional VR world may be rendered around the avatar. IK/rendering engine 630 may animate the surface of an avatar with movement according to, e.g., one or more of vertex animation and skeletal deformation. The rendering of the avatar and three-dimensional VR world is produced for the patient to see so that the patient may participate in activities in the VR world. For instance, IK/rendering engine 630 may generate stereoscopic views in each corresponding eye display of an HMD.

At step 636, IK/rendering engine 630 generates a reproduction of Patient View and transmits the reproduction. For instance, IK/rendering engine 630 creates a Spectator View and transmits Spectator View to, e.g., a supervisor engine 640 running on a clinician tablet. Scenario 100 of FIG. 1 depicts an embodiment of Spectator View. In some embodiments, IK/rendering engine 630 may generate a 2D composite view of the stereoscopic views produced for each corresponding eye display of an HMD and relay the composite display, e.g., to a clinician tablet for display. In some embodiments, IK/rendering engine 630 may take one of the displays of the stereoscopic views produced for each corresponding eye display of an HMD and transmit the one display for use as a Spectator View.

At step 642, supervisor engine 640 displays first-person Spectator View from the reproduced Patient View. Supervisor engine 640 may be incorporated in a clinician tablet, such as clinician tablet 210 as depicted in FIG. 7A. Spectator View may be a reproduction or mirroring of the visual display in the headset. Spectator View may be, for example, a two-dimensional version of Patient View, displayed on a clinician tablet or even using a separate, larger display screen for multiple therapists or spectators. Spectator View is vital for monitoring by a supervisor or therapist who may aid the patient in comprehending and performing the therapeutic activity. Scenario 100 of FIG. 1 depicts an example of Spectator View.

At step 644, supervisor engine 640 generates a third-person view, Live Avatar View (LAV), of an avatar from skeletal data. For instance, LAV may be a third-person view of a rendered three-dimensional avatar configured to mimic a patient's movements based on provided avatar skeletal data. Scenario 200 of FIG. 2 and Scenario 400 of FIG. 4 each depict an example of a Live Avatar View that may allow a therapist to monitor movements of the patient's avatar to ensure proper interaction with the virtual world, as well as patient safety. An avatar in LAV may be a rudimentary avatar rendering without skin, features, or customizations based on size and weight. An avatar may be rendered as translucent. For instance, an avatar in LAV may be a featureless, translucent blue model that mimics patient movement. In some embodiments, translucency of the avatar may be adjustable with a supervisor setting. Movements of the avatar are based on skeletal data provided by IK/rendering engine 630. In some embodiments, a real-time 3D engine, such as Babylon.js, may render 3D graphics, e.g., in a web browser on a clinician tablet based on received skeletal data from the Unreal Engine stored and executed on an HMD. In some embodiments, activity data may be transmitted with skeletal data and the generated LAV may include activity cues such as activity arrow 250 in Scenario 200 of FIG. 2 and bubbles 442-452 of Scenario 400 of FIG. 4.

At step 646, supervisor engine 640 overlays the translucent LAV over Spectator View. For instance, supervisor engine 640 layers multiple views with LAV on top of the Spectator View. In some embodiments, supervisor engine 640 generates a Dual Perspective View and renders a translucent avatar from Live Avatar View to overlay the Spectator View during a therapy session. In Dual Perspective View, for example, a translucent avatar may be rendered over the Spectator View. Scenarios 300 and 500 each depict examples of Dual Perspective View. In some embodiments, the avatar itself is translucent and Spectator View is generally visible. In some embodiments, e.g., when activity cues or other information may be depicted, layering may include graying out Spectator View by displaying a gray mask with low alpha channel to better distinguish each layer.

At step 648, supervisor engine 640 displays Dual Perspective View as a multi-view overlay. In Dual Perspective View, a translucent avatar of LAV may be rendered over the Spectator View, and both views can be maximized on the tablet, visible together. In some embodiments, one or more layers may be shaded or colored to better distinguish each layer from another. In some embodiments, Dual Perspective View may depict various activity cues and/or allow for multiple layers of views.

FIG. 7A is a diagram of an illustrative system, in accordance with some embodiments of the disclosure. A VR system may include a clinician tablet 210, head-mounted display 201 (HMD or headset), small sensors 202, and large sensor 202B. Large sensor 202B may comprise transmitters, in some embodiments, and be referred to as wireless transmitter module 202B. Some embodiments may include sensor chargers, router, router battery, headset controller, power cords, USB cables, and other VR system equipment.

Clinician tablet 210 may be configured to use a touch screen, a power/lock button that turns the component on or off, and a charger/accessory port, e.g., USB-C. For instance, pressing the power button on clinician tablet 210 may power on the tablet or restart the tablet. Once clinician tablet 210 is powered on, a therapist or supervisor may access a user interface and be able to log in; add or select a patient; initialize and sync sensors; select, start, modify, or end a therapy session; view data; and/or log out.

Headset 201 may comprise a power button that turns the component on or off, as well as a charger/accessory port, e.g., USB-C. Headset 201 may also provide visual feedback of virtual reality applications in concert with the clinician tablet and the small and large sensors.

Charging headset 201 may be performed by plugging a headset power cord into the storage dock or an outlet. To turn on headset 201 or restart headset 201, the power button may be pressed. A power button may be on top of the headset. Some embodiments may include a headset controller used to access system settings. For instance, a headset controller may be used only in certain troubleshooting and administrative tasks and not necessarily during patient therapy. Buttons on the controller may be used to control power, connect to headset 201, access settings, or control volume.

The large sensor 202B and small sensors 202 are equipped with mechanical and electrical components that measure position and orientation in physical space and then translate that information to construct a virtual environment. Sensors 202 are turned off and charged when placed in the charging station. Sensors 202 turn on and attempt to sync when removed from the charging station. The sensor charger acts as a dock to store and charge the sensors. In some embodiments, sensors may be placed in sensor bands on a patient. Sensor bands 205, as depicted in FIGS. 7B-C, are typically required for use and are provided separately for each patient for hygienic purposes. In some embodiments, sensors may be miniaturized and may be placed, mounted, fastened, or pasted directly onto a user.

As shown in illustrative FIG. 7A, various systems disclosed herein consist of a set of position and orientation sensors that are worn by a VR participant, e.g., a therapy patient. These sensors communicate with HMD 201, which immerses the patient in a VR experience. An HMD suitable for VR often comprises one or more displays to enable stereoscopic three-dimensional (3D) images. Such internal displays are typically high-resolution (e.g., 2880×1600 or better) and offer high refresh rate (e.g., 75 Hz). The displays are configured to present 3D images to the patient. VR headsets typically include speakers and microphones for deeper immersion.

HMD 201 is a piece central to immersing a patient in a virtual world in terms of presentation and movement. A headset may allow, for instance, a wide field of view (e.g., 110°) and tracking along six degrees of freedom. HMD 201 may include cameras, accelerometers, gyroscopes, and proximity sensors. VR headsets typically include a processor, usually in the form of a system on a chip (SoC), and memory. In some embodiments, headsets may also use, for example, additional cameras as safety features to help users avoid real-world obstacles. HMD 201 may comprise more than one connectivity option in order to communicate with the therapist's tablet. For instance, an HMD 201 may use an SoC that features WiFi and Bluetooth connectivity, in addition to an available USB connection (e.g., USB Type-C). The USB-C connection may also be used to charge the built-in rechargeable battery for the headset.

A supervisor, such as a health care provider or therapist, may use a tablet, e.g., tablet 210 depicted in FIG. 7A, to control the patient's experience. In some embodiments, tablet 210 runs an application and communicates with a router to cloud software configured to authenticate users and store information. Tablet 210 may communicate with HMD 201 in order to initiate HMD applications, collect relayed sensor data, and update records on the cloud servers. Tablet 210 may be stored in the portable container and plugged in to charge, e.g., via a USB plug.

In some embodiments, such as depicted in FIGS. 7B-C, sensors 202 are placed on the body in particular places to measure body movement and relay the measurements for translation and animation of a VR avatar. Sensors 202 may be strapped to a body via bands 205. In some embodiments, each patient may have her own set of bands 205 to minimize hygiene issues.

A wireless transmitter module (WTM) 202B may be worn on a sensor band 205B that is laid over the patient's shoulders. WTM 202B sits between the patient's shoulder blades on their back. Wireless sensor modules 202 (e.g., sensors or WSMs) are worn just above each elbow, strapped to the back of each hand, and on a pelvis band that positions a sensor adjacent to the patient's sacrum on their back. In some embodiments, each WSM communicates its position and orientation in real-time with an HMD Accessory located on the HMD. Each sensor 202 may learn its relative position and orientation to the WTM, e.g., via calibration.

The HMD accessory may include a sensor 202A that may allow it to learn its position relative to WTM 202B, which then allows the HMD to know where in physical space all the WSMs and WTM are located. In some embodiments, each sensor 202 communicates independently with the HMD accessory which then transmits its data to HMD 201, e.g., via a USB-C connection. In some embodiments, each sensor 202 communicates its position and orientation in real-time with WTM 202B, which is in wireless communication with HMD 201.

A VR environment rendering engine on HMD 201 (sometimes referred to herein as a "VR application"), such as the Unreal Engine™, uses the position and orientation data to create an avatar that mimics the patient's movement.

A patient or player may "become" their avatar when they log in to a virtual reality game. When the player moves their body, they see their avatar move accordingly. Sensors in the headset may allow the patient to move the avatar's head, e.g., even before body sensors are placed on the patient. A system that achieves consistent high-quality tracking facilitates the patient's movements to be accurately mapped onto an avatar.

Sensors 202 may be placed on the body, e.g., of a patient by a therapist, in particular locations to sense and/or translate body movements. The system can use measurements of position and orientation of sensors placed in key places to determine movement of body parts in the real world and translate such movement to the virtual world. In some embodiments, a VR system may collect data for therapeutic analysis of a patient's movements and range of motion.

In some embodiments, systems and methods of the present disclosure may use electromagnetic tracking, optical tracking, infrared tracking, accelerometers, magnetometers, gyroscopes, myoelectric tracking, other tracking techniques, or a combination of one or more of such tracking methods. The tracking systems may be parts of a computing system as disclosed herein. The tracking tools may exist on one or more circuit boards within the VR system (see FIG. 9) where they may monitor one or more users to perform one or more functions such as capturing, analyzing, and/or tracking a subject's movement. In some cases, a VR system may utilize more than one tracking method to improve reliability, accuracy, and precision.

Figure 8A:
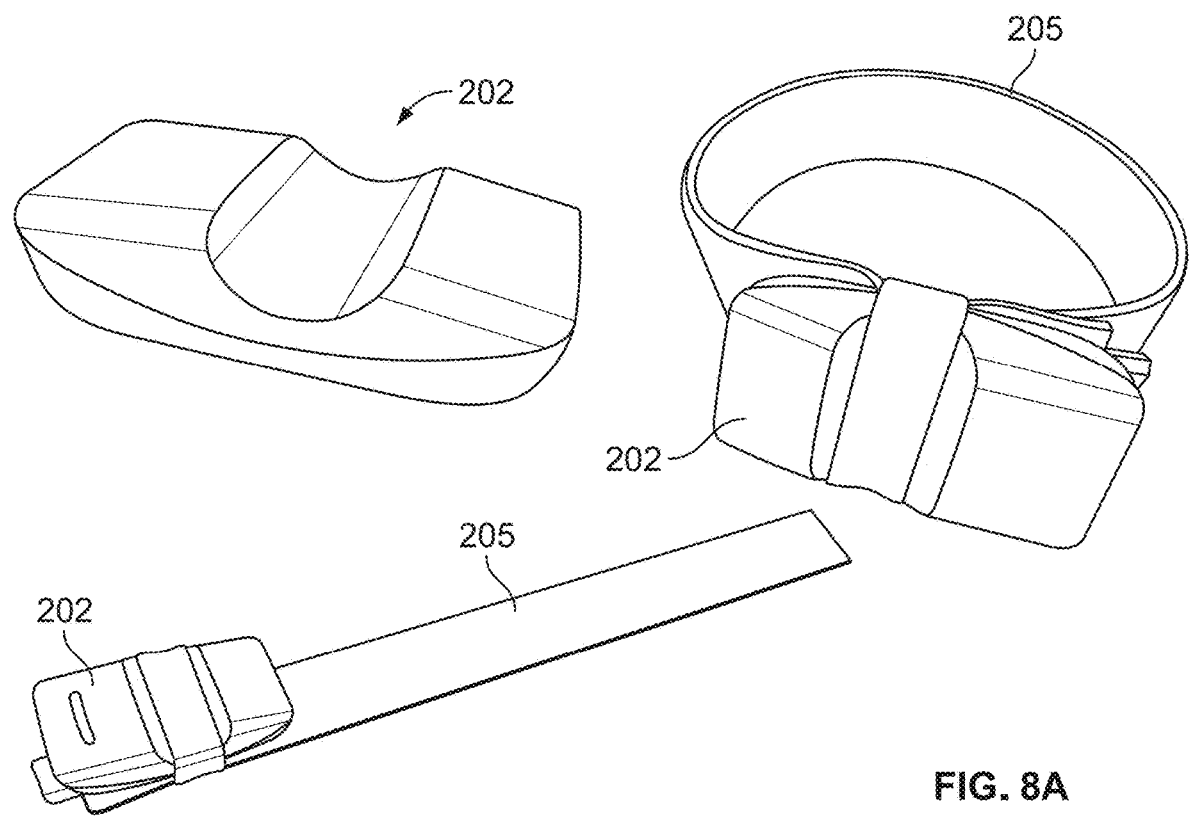
FIG. 8A is a diagram of an illustrative system, in accordance with some embodiments of the disclosure.
Figure 8B:
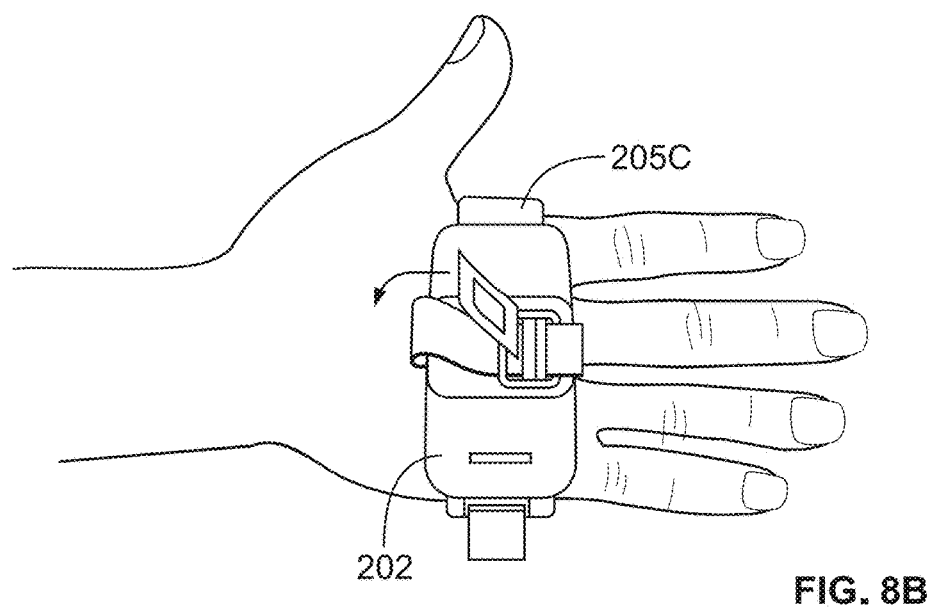
FIG. 8B is a diagram of an illustrative system, in accordance with some embodiments of the disclosure.

FIGS. 8A-C illustrate examples of wearable sensors 202 and bands 205. In some embodiments, bands 205 may include elastic loops to hold the sensors. In some embodiments, bands 205 may include additional loops, buckles and/or Velcro straps to hold the sensors. For instance, bands 205 for hands may require extra secureness as a patient's hands may be moved at a greater speed and could throw or project a sensor in the air if it is not securely fastened. FIG. 2C illustrates an exemplary embodiment with a slide buckle.

Sensors 202 may be attached to body parts via band 205. In some embodiments, a therapist attaches sensors 202 to proper areas of a patient's body. For example, a patient may not be physically able to attach band 205 to herself. In some embodiments, each patient may have her own set of bands 205 to minimize hygiene issues. In some embodiments, a therapist may bring a portable case to a patient's room or home for therapy. The sensors may include contact ports for charging each sensor's battery while storing and transporting in the container, such as the container depicted in FIG. 7A.

As illustrated in FIG. 8C, sensors 202 are placed in bands 205 prior to placement on a patient. In some embodiments, sensors 202 may be placed onto bands 205 by sliding them into the elasticized loops. The large sensor, WTM 202B, is placed into a pocket of shoulder band 205B. Sensors 202 may be placed above the elbows, on the back of the hands, and at the lower back (sacrum). In some embodiments, sensors may be used at the knees and/or ankles. Sensors 202 may be placed, e.g., by a therapist, on a patient while the patient is sitting on a bench (or chair) with his hands on his knees. Sensor band 205D to be used as a hip sensor 202 has a sufficient length to encircle a patient's waist.

Once sensors 202 are placed in bands 205, each band may be placed on a body part, e.g., according to FIG. 7C. In some embodiments, shoulder band 205B may require connection of a hook and loop fastener. An elbow band 205 holding a sensor 202 should sit behind the patient's elbow. In some embodiments, hand sensor bands 205C may have one or more buckles to, e.g., fasten sensors 202 more securely, as depicted in FIG. 8B.

Each of sensors 202 may be placed at any of the suitable locations, e.g., as depicted in FIG. 7C. After sensors 202 have been placed on the body, they may be assigned or calibrated for each corresponding body part.

Generally, sensor assignment may be based on the position of each sensor 202. Sometimes, such as cases where patients have varying height discrepancies, assigning a sensor merely based on height is not practical. In some embodiments, sensor assignment may be based on relative position to, e.g., wireless transmitter module 202B.

Figure 9:
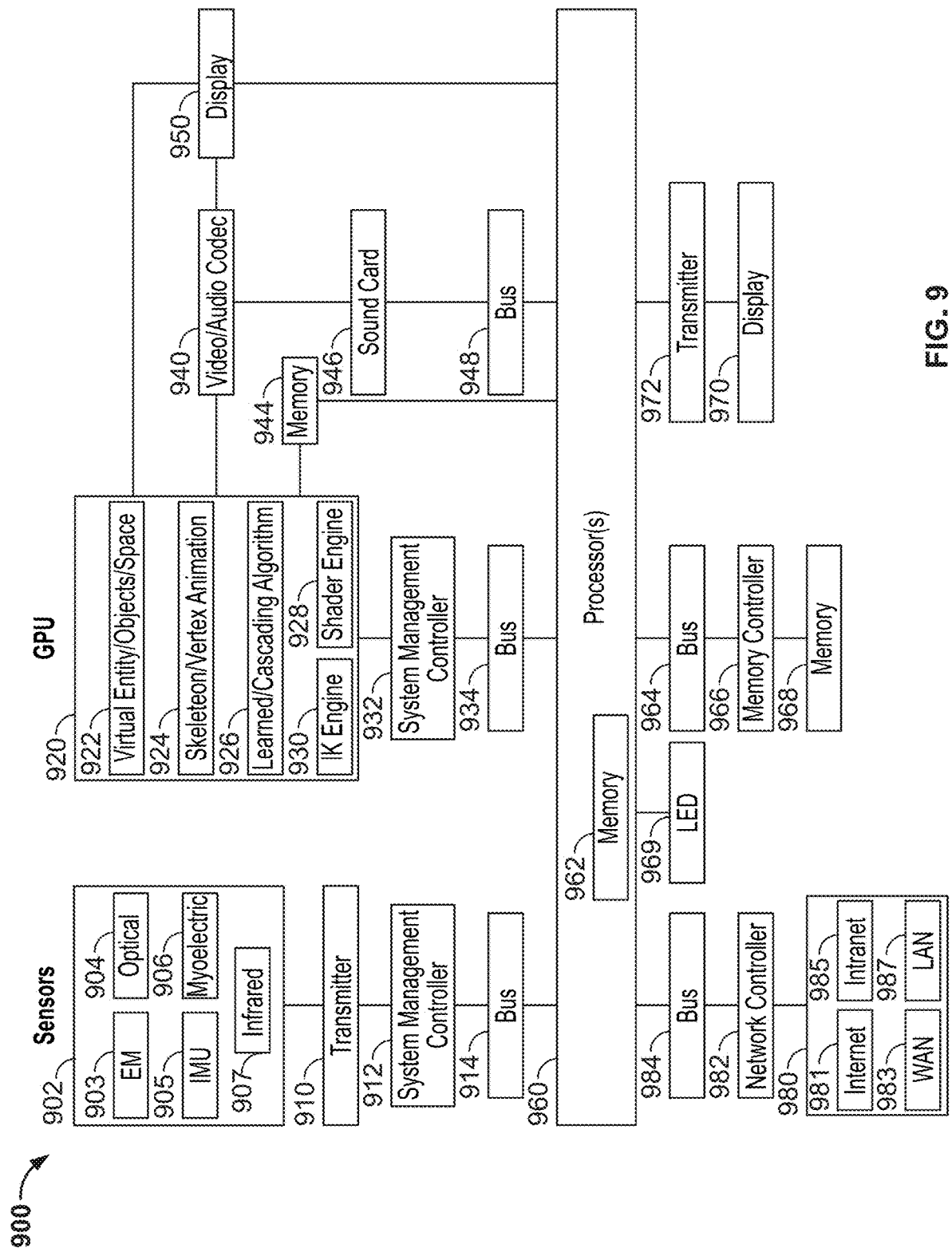
FIG. 9 is a diagram of an illustrative system, in accordance with some embodiments of the disclosure.

FIG. 9 depicts an illustrative arrangement for various elements of a system, e.g., an HMD and sensors of FIGS. 7A-D. The arrangement includes one or more printed circuit boards (PCBs). In general terms, the elements of this arrangement track, model, and display a visual representation of the participant (e.g., a patient avatar) in the VR world by running software including the aforementioned VR application of HMD 201.

The arrangement shown in FIG. 9 includes one or more sensors 902, processors 960, graphic processing units (GPUs) 920, video encoder/video codec 940, sound cards 946, transmitter modules 910, network interfaces 980, and light emitting diodes (LEDs) 969. These components may be housed on a local computing system or may be remote components in wired or wireless connection with a local computing system (e.g., a remote server, a cloud, a mobile device, a connected device, etc.). Connections between components may be facilitated by one or more buses, such as bus 914, bus 934, bus 948, bus 984, and bus 964 (e.g., peripheral component interconnects (PCI) bus, PCI-Express bus, or universal serial bus (USB)). With such buses, the computing environment may be capable of integrating numerous components, numerous PCBs, and/or numerous remote computing systems.

One or more system management controllers, such as system management controller 912 or system management controller 932, may provide data transmission management functions between the buses and the components they integrate. For instance, system management controller 912 provides data transmission management functions between bus 914 and sensors 902. System management controller 932 provides data transmission management functions between bus 934 and GPU 920. Such management controllers may facilitate the arrangements orchestration of these components that may each utilize separate instructions within defined time frames to execute applications. Network interface 980 may include an ethernet connection or a component that forms a wireless connection, e.g., 802.11b, g, a, or n connection (WiFi), to a local area network (LAN) 987, wide area network (WAN) 983, intranet 985, or internet 981. Network controller 982 provides data transmission management functions between bus 984 and network interface 980.

Processor(s) 960 and GPU 920 may execute a number of instructions, such as machine-readable instructions. The instructions may include instructions for receiving, storing, processing, and transmitting tracking data from various sources, such as electromagnetic (EM) sensors 903, optical sensors 904, infrared (IR) sensors 907, inertial measurement units (IMUs) sensors 905, and/or myoelectric sensors 906. The tracking data may be communicated to processor(s) 960 by either a wired or wireless communication link, e.g., transmitter 910. Upon receiving tracking data, processor(s) 960 may execute an instruction to permanently or temporarily store the tracking data in memory 962 such as, e.g., random access memory (RAM), read only memory (ROM), cache, flash memory, hard disk, or other suitable storage component. Memory may be a separate component, such as memory 968, in communication with processor(s) 960 or may be integrated into processor(s) 960, such as memory 962, as depicted.

Processor(s) 960 may also execute instructions for constructing an instance of virtual space. The instance may be hosted on an external server and may persist and undergo changes even when a participant is not logged in to said instance. In some embodiments, the instance may be participant-specific, and the data required to construct it may be stored locally. In such an embodiment, new instance data may be distributed as updates that users download from an external source into local memory. In some exemplary embodiments, the instance of virtual space may include a virtual volume of space, a virtual topography (e.g., ground, mountains, lakes), virtual objects, and virtual characters (e.g., non-player characters "NPCs"). The instance may be constructed and/or rendered in 2D or 3D. The rendering may offer the viewer a first-person or third-person perspective. A first-person perspective may include displaying the virtual world from the eyes of the avatar and allowing the patient to view body movements from the avatar's perspective. A third-person perspective may include displaying the virtual world from, for example, behind the avatar to allow someone to view body movements from a different perspective. The instance may include properties of physics, such as gravity, magnetism, mass, force, velocity, and acceleration, which cause the virtual objects in the virtual space to behave in a manner at least visually similar to the behaviors of real objects in real space.

Processor(s) 960 may execute a program (e.g., the Unreal Engine or VR applications discussed above) for analyzing and modeling tracking data. For instance, processor(s) 960 may execute a program that analyzes the tracking data it receives according to algorithms described above, along with other related pertinent mathematical formulas. Such a program may incorporate a graphics processing unit (GPU) 920 that is capable of translating tracking data into 3D models. GPU 920 may utilize shader engine 928, vertex animation 924, and linear blend skinning algorithms. In some instances, processor(s) 960 or a CPU may at least partially assist the GPU in making such calculations. This allows GPU 920 to dedicate more resources to the task of converting 3D scene data to the projected render buffer. GPU 920 may refine the 3D model by using one or more algorithms, such as an algorithm learned on biomechanical movements, a cascading algorithm that converges on a solution by parsing and incrementally considering several sources of tracking data, an inverse kinematics (IK) engine 930, a proportionality algorithm, and other algorithms related to data processing and animation techniques. After GPU 920 constructs a suitable 3D model, processor(s) 960 executes a program to transmit data for the 3D model to another component of the computing environment (or to a peripheral component in communication with the computing environment) that is capable of displaying the model, such as display 950.

In some embodiments, GPU 920 transfers the 3D model to a video encoder or a video codec 940 via a bus, which then transfers information representative of the 3D model to a suitable display 950. The 3D model may be representative of a virtual entity that can be displayed in an instance of virtual space, e.g., an avatar. The virtual entity is capable of interacting with the virtual topography, virtual objects, and virtual characters within virtual space. The virtual entity is controlled by a user's movements, as interpreted by sensors 902 communicating with the system. Display 950 may display a Patient View. The patient's real-world movements are reflected by the avatar in the virtual world. The virtual world may be viewed in the headset in 3D and monitored on the tablet in two dimensions. In some embodiments, the VR world is a game that provides feedback and rewards based on the patient's ability to complete activities. Data from the in-world avatar is transmitted from the HMD to the tablet to the cloud, where it is stored for later analysis. An illustrative architectural diagram of such elements in accordance with some embodiments is depicted in FIG. 10.

A VR system may also comprise display 970, which is connected to the computing environment via transmitter 972. Display 970 may be a component of a clinician tablet. For instance, a supervisor or operator, such as a therapist, may securely log in to a clinician tablet, coupled to the system, to observe and direct the patient to participate in various activities and adjust the parameters of the activities to best suit the patient's ability level. Display 970 may depict at least one of a Spectator View, Live Avatar View, or Dual Perspective View.

Figure 10:
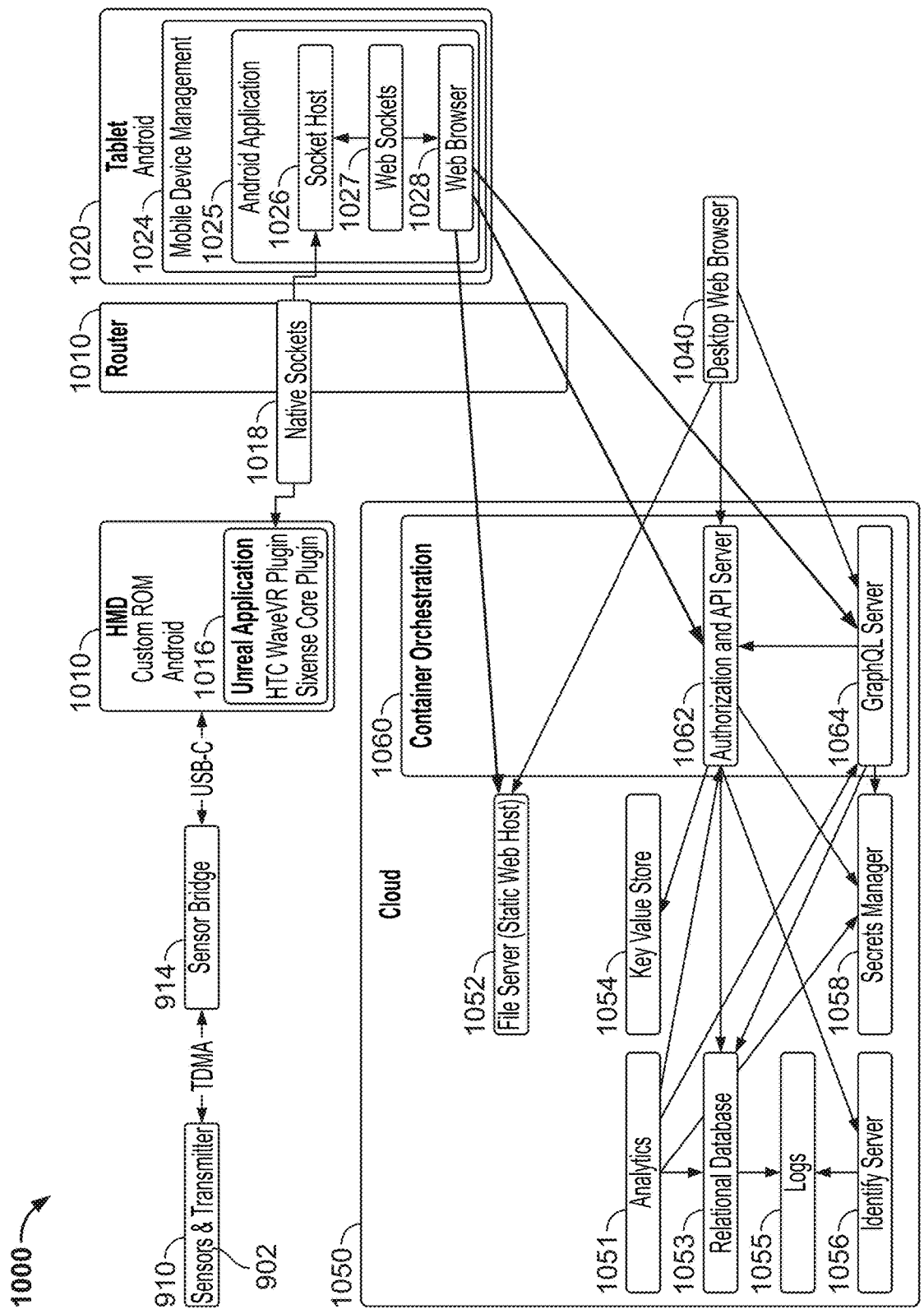
FIG. 10 is a diagram of an illustrative system, in accordance with some embodiments of the disclosure.

In some embodiments, HMD 201 may be the same as or similar to HMD 1010 in FIG. 10. In some embodiments, HMD 1010 runs a version of Android that is provided by HTC (e.g., a headset manufacturer) and the VR application is an Unreal application, e.g., Unreal Application 1016, encoded in an Android package (.apk). The .apk comprises a set of custom plugins: WVR, WaveVR, SixenseCore, SixenseLib, and MVICore. The WVR and WaveVR plugins allow the Unreal application to communicate with the VR headset's functionality. The SixenseCore, SixenseLib, and MVICore plugins allow Unreal Application 1016 to communicate with the HMD accessory and sensors that communicate with the HMD via USB-C. The Unreal Application comprises code that records the position and orientation (P&O) data of the hardware sensors and translates that data into a patient avatar, which mimics the patient's motion within the VR world. An avatar can be used, for example, to infer and measure the patient's real-world range of motion. The Unreal application of the HMD includes an avatar solver as described, for example, below.

The operator device, clinician tablet 1020, runs a native application (e.g., Android application 1025) that allows an operator such as a therapist to control a patient's experience. Cloud server 1050 includes a combination of software that manages authentication, data storage and retrieval, and hosts the user interface, which runs on the tablet. This can be accessed by tablet 1020. Tablet 1020 has several modules.

As depicted in FIG. 10, the first part of tablet software is a mobile device management (MDM) 1024 layer, configured to control what software runs on the tablet, enable/disable the software remotely, and remotely upgrade the tablet applications.

The second part is an application, e.g., Android Application 1025, configured to allow an operator to control the software of HMD 1010. In some embodiments, the application may be a native application. A native application, in turn, may comprise two parts, e.g., (1) socket host 1026 configured to receive native socket communications from the HMD and translate that content into web sockets, e.g., web sockets 1027, that a web browser can easily interpret; and (2) a web browser 1028, which is what the operator sees on the tablet screen. The web browser may receive data from the HMD via the socket host 1026, which translates the HMD's native socket communication 1018 into web sockets 1027, and it may receive UI/UX information from a file server 1052 in cloud 1050. Tablet 1020 comprises web browser 1028, which may incorporate a real-time 3D engine, such as Babylon.js, using a JavaScript library for displaying 3D graphics in web browser 1028 via HTML5. For instance, a real-time 3D engine, such as Babylon.js, may render 3D graphics, e.g., in web browser 1028 on clinician tablet 1020, based on received skeletal data from an avatar solver in the Unreal Engine 1016 stored and executed on HMD 1010. In some embodiments, rather than Android Application 1026, there may be a web application or other software to communicate with file server 1052 in cloud 1050. In some instances, an application of Tablet 1020 may use, e.g., Web Real-Time Communication (WebRTC) to facilitate peer-to-peer communication without plugins, native apps, and/or web sockets.

The cloud software, e.g., cloud 1050, has several different, interconnected parts configured to communicate with the tablet software: authorization and API server 1062, GraphQL server 1064, and file server (static web host) 1052.

In some embodiments, authorization and API server 1062 may be used as a gatekeeper. For example, when an operator attempts to log in to the system, the tablet communicates with the authorization server. This server ensures that interactions (e.g., queries, updates, etc.) are authorized based on session variables such as operator's role, the health care organization, and the current patient. This server, or group of servers, communicates with several parts of the system: (a) a key value store 1054, which is a clustered session cache that stores and allows quick retrieval of session variables; (b) a GraphQL server 1064, as discussed below, which is used to access the back-end database in order to populate the key value store, and also for some calls to the application programming interface (API); (c) an identity server 1056 for handling the user login process; and (d) a secrets manager 1058 for injecting service passwords (relational database, identity database, identity server, key value store) into the environment in lieu of hard coding.

When the tablet requests data, it will communicate with the GraphQL server 1064, which will, in turn, communicate with several parts: (1) the authorization and API server 1062; (2) the secrets manager 1058, and (3) a relational database 1053 storing data for the system. Data stored by the relational database 1053 may include, for instance, profile data, session data, game data, and motion data.

In some embodiments, profile data may include information used to identify the patient, such as a name or an alias. Session data may comprise information about the patient's previous sessions, as well as, for example, a "free text" field into which the therapist can input unrestricted text, and a log 1055 of the patient's previous activity. Logs 1055 are typically used for session data and may include, for example, total activity time, e.g., how long the patient was actively engaged with individual activities; activity summary, e.g., a list of which activities the patient performed, and how long they engaged with each on; and settings and results for each activity. Game data may incorporate information about the patient's progression through the game content of the VR world. Motion data may include specific range-of-motion (ROM) data that may be saved about the patient's movement over the course of each activity and session, so that therapists can compare session data to previous sessions' data.

In some embodiments, file server 1052 may serve the tablet software's website as a static web host.

While the foregoing discussion describes exemplary embodiments of the present invention, one skilled in the art will recognize from such discussion, the accompanying drawings, and the claims, that various modifications can be made without departing from the spirit and scope of the invention. Therefore, the illustrations and examples herein should be construed in an illustrative, and not a restrictive sense. The scope and spirit of the invention should be measured solely by reference to the claims that follow.

What is claimed is:

1. A method for generating a dual perspective display to monitor a virtual reality environment, the method comprising:
   receiving a first-person display in the virtual reality environment;
   receiving avatar skeleton data;
   generating a second display by rendering a translucent avatar based on the avatar skeleton data; and
   generating for display the dual perspective display by overlaying the second display over the first-person display in the virtual reality environment.

2. The method of claim 1, wherein the first-person display is generated by a headset, comprising:
   receiving sensor data;
   converting the sensor data to avatar skeleton data; and
   rendering the first-person display based on the avatar skeleton data.

3. The method of claim 2, wherein the first-person display and avatar skeleton data are transmitted from the headset.

4. The method of claim 2, wherein the first-person display is rendered by a virtual reality environment rendering engine.

5. The method of claim 4, wherein the virtual reality environment rendering engine comprises a three-dimensional environment developing platform.

6. The method of claim 2, wherein the translucent avatar is rendered by a real-time three-dimensional engine for displaying three-dimensional graphics in a web browser.

7. The method of claim 2, wherein the receiving sensor data further includes receiving position and orientation data from a plurality of sensors placed a virtual reality participant's body and wherein converting the sensor data to avatar skeleton data further includes generating avatar skeletal data based on the position and orientation data from the plurality of sensors.

8. The method of claim 1, wherein the second display is a third-person view of the translucent avatar.

9. The method of claim 1 further comprising receiving activity information including activity cues.

10. The method of claim 9 further comprising rendering activity cues in the second display as at least one indication of a direction to look.

11. The method of claim 9, wherein the activity cues comprise virtual object locations.

12. The method of claim 2, wherein the first-person display is transmitted from the headset to a tablet.

13. The method of claim 12, wherein the transmission is at least one of the following connection types: WiFi and Bluetooth.

14. The method of claim 1, wherein the dual perspective display is part of a user interface that includes patient data and activity data.

15. The method of claim 1, wherein the dual perspective display comprises a filter for the first-person display to distinguish the second display.

16. The method of claim 1, wherein the translucent avatar changes degree of transparency based on selective adjustment of a transparency setting.

17. A system of generating a dual perspective display to monitor a virtual reality environment, the system comprising:
input/output computer processor circuitry configured to:
receive a first-person display;
receive avatar skeleton data; and
processing circuitry configured to:
generate a second display by rendering a translucent avatar based on the avatar skeleton data; and
generate for display the dual perspective display by overlaying the second display over the first-person display in the virtual reality environment.

18. The system of claim 17, wherein the first-person display is generated by a headset comprising second input/output circuitry configured to receive sensor data; and
second processing circuitry configured to convert the sensor data to avatar skeleton data and render the first-person display based on the avatar skeleton data.

19. The system of claim 18, wherein the second input/output circuitry is further configured to transmit the first-person display and avatar skeleton data from the headset.

20. The system of claim 18, wherein the second processing circuitry is further configured to use a virtual reality environment rendering engine to render the first-person display.

* * * * *